(12) United States Patent
Baldwin

(10) Patent No.: US 8,217,161 B2
(45) Date of Patent: Jul. 10, 2012

(54) METHODS OF INHIBITING MULTIPLE CYTOCHROME P450 GENES WITH SIRNA

(75) Inventor: William S. Baldwin, Seneca, SC (US)

(73) Assignee: Clemson University Research Foundation, Clemson, SC (US)

( * ) Notice: Subject to any disclaimer, the term of this patent is extended or adjusted under 35 U.S.C. 154(b) by 412 days.

(21) Appl. No.: 12/427,791

(22) Filed: Apr. 22, 2009

(65) Prior Publication Data

US 2009/0265795 A1    Oct. 22, 2009

Related U.S. Application Data

(60) Provisional application No. 61/046,937, filed on Apr. 22, 2008.

(51) Int. Cl.
*C07H 21/02* (2006.01)
*C07H 21/04* (2006.01)
*C12Q 1/68* (2006.01)
*C12N 5/02* (2006.01)
*C12N 15/11* (2006.01)

(52) U.S. Cl. ....... 536/24.5; 536/23.1; 435/6.1; 435/325; 514/44 A

(58) Field of Classification Search .......... None
See application file for complete search history.

(56) References Cited

U.S. PATENT DOCUMENTS

2004/0010809 A1* 1/2004 Wolf et al. ............ 800/3
2004/0096882 A1* 5/2004 Gleave et al. ......... 435/6
2006/0212950 A1* 9/2006 Tuschl et al. ......... 800/14
2007/0244312 A1  10/2007 Khvorova et al.

FOREIGN PATENT DOCUMENTS

WO    WO 2005/001092 A2 *  1/2005

OTHER PUBLICATIONS

Anderson et al., Oligonucleotides (2003) 13:303-312.*
R. Acevedo et al., "The contribution of hepatic steroid metabolism to serum estradiol and estriol concentrations in nonylphenol treated MMTVneu mice and its potential effects on breast cancer incidence and latency", Journal of Applied Toxicology, vol. 25, pp. 339-353 (2005).
C. Cheung et al., "Growth Hormone Determines Sexual Dimorphism of Hepatic Cytochrome P450 3A4 Expression in Transgenic Mice", The Journal of Pharmacology and Experimental Therapeutics, vol. 316:3, pp. 1328-1334 (2006).
J.P. Hernandez et al., "The Environmental Estrogen, Nonylphenol, Activates the Constitutive Androstane Receptor", Toxicological Sciences, vol. 98:2, pp. 416-426 (2007).
J.P. Hernandez et al., "Gender-specific induction of cytochrome P450s in nonylphenol-treated FVB/NJ mice", Toxicology and Applied Pharmacology, vol. 216, pp. 186-196 (2006).
Kretschmer et al., "CAR and PXR: Xenosensors of endocrine disrupters?", Chemico-Biological Interactions, vol. 155, pp. 111-128 (2005).
A.E. van Herwaarden et al., "Knockout of cytochrome P450 3A yields new mouse models for understanding xenobiotic metabolism", The Journal of Clinical Investigation, vol. 117:11, pp. 3583-3592 (Nov. 2007).

* cited by examiner

*Primary Examiner* — Doug Schultz
(74) *Attorney, Agent, or Firm* — Dority & Manning, P.A.

(57) ABSTRACT

The present invention relates to siRNAs that are targeted to RNAs encoding two or more enzymes of a subfamily of cytochrome P450 (CYP) enzymes, along with vectors, cells, and kits comprising the siRNAs. The invention further relates to methods of decreasing expression of two or more CYP subfamily genes in a non-human animal, animals in which expression of two or more CYP subfamily genes has been decreased, and methods of using such animals to study the function of cytochrome P450 enzymes.

28 Claims, 3 Drawing Sheets

FIG. 1

```
Cyp2b9  NM_010000.2|    KD1         TCCAAAAGGAGAGATTGATCAGGTGATCGGCTCACACCGGCTACCAACTCTT 1045 (SEQ ID NO:33)
Cyp2b13 NM_007813.1|                TCCAAAAGGAGAGATTGATCAGGTGATCGGCTCACACCGGCTACCAACCCTT 1045 (SEQ ID NO:34)
Cyp2b23 NM_001081148.                TCCAAAAGGAGAGATTGATCAGGTGATCAGTGCACACCATGTCCAACCCTT  1020 (SEQ ID NO:35)
Cyp2b10 AK028103.1|                 TCCAAAAGGAGAGATTGATCAGGTGATCGGCTCACACCGGCTACCAACCCTT 1047 (SEQ ID NO:36)
Cyp2b19 AF047529.1|AF047            TCCAAAAGGAGAGATTGATCAGGTGATCGGCTCACACCGGCTACCGACTCTT 1023 (SEQ ID NO:37)
*CYP2B6-human NM_000767.4|          TCTACAGGGAGATTGAACAGGTGATTGGCCCACATGCCCCTCCAGAGCTT   1027 (SEQ ID NO:38)
                                    ** * * ********* ********    * *****   * *** ***

Cyp2b9  NM_010000.2|    KD2         ACACACTGTTCCGAGGGTACCTGCTCCCCAAGAACACTGAGGTGTACCCC   1195 (SEQ ID NO:39)
Cyp2b13 NM_007813.1|                ATACCATGTTCCGAGGGTACCTGCTCCCCAAGAACACTGAGGTGTACCCC   1195 (SEQ ID NO:40)
Cyp2b23 NM_001081148.                ACACAGTGTTCCGAGGATACCTGCTCCCCAAGAACACTGAGGTGTACCCC   1170 (SEQ ID NO:41)
Cyp2b10 AK028103.1|                 ATACCATGTTCCGAGGATACCTGCTCCCCAAGAACACTGAGGTGTACCCC   1197 (SEQ ID NO:42)
Cyp2b19 AF047529.1|AF047            ACACACTGTTCCGAGAGATACCTGATCCCCAAGAACACTGAGGTGTACCCC  1173 (SEQ ID NO:43)
*CYP2B6-human NM_000767.4|          ACACCAGCTTCCGAGGGTACATCATCCCCAAGGACACAGAAGTATTTCTC   1177 (SEQ ID NO:44)
                                    * ** ********* *** ** * *******  *** ** **   **

Cyp2b9  NM_010000.2|    KD3         AAGCTTTTCTGCCCTTCTCCAAGGAAAGCGCATTTGTCTTGGTGAAAGC    1345 (SEQ ID NO:45)
Cyp2b13 NM_007813.1|                AAGCTTTTCTACCCTTCTCCAAGGAAAGCGCATTTGTCTTGGTGAAAGC    1345 (SEQ ID NO:46)
Cyp2b23 NM_001081148.                AAGCTTTTCTGCCCTTCTCCAAGGAAAGCGCATTTGTCTTGCCGAAGGC    1320 (SEQ ID NO:47)
Cyp2b10 AK028103.1|                 AAGCTTTTCTGCCCTTCTCAACAGGAAAGCGCATTTGTCTTGGTGAAAGC   1347 (SEQ ID NO:48)
Cyp2b19 AF047529.1|AF047            AAGCTTTCATGCCCTTCTCCAAGGAAAGCGCATTTGTCTTGGAGAAGGC    1323 (SEQ ID NO:49)
*CYP2B6-human NM_000767.4|          AAGCTTTTATCCCCTTCTCTTAGGGAAGCGGATTTGTCTTGGTGAAGGC    1327 (SEQ ID NO:50)
                                    ******** *  ********    *  ****** ************ *** **
```

FIG. 3
A
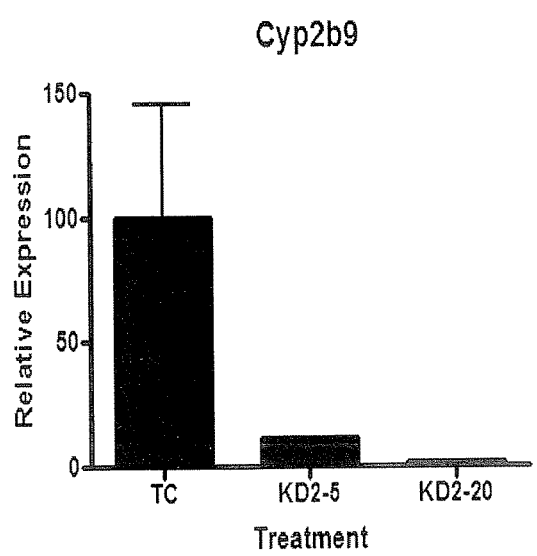
B
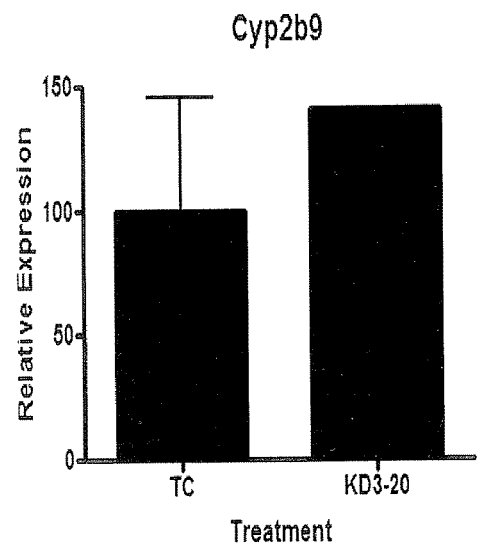
C
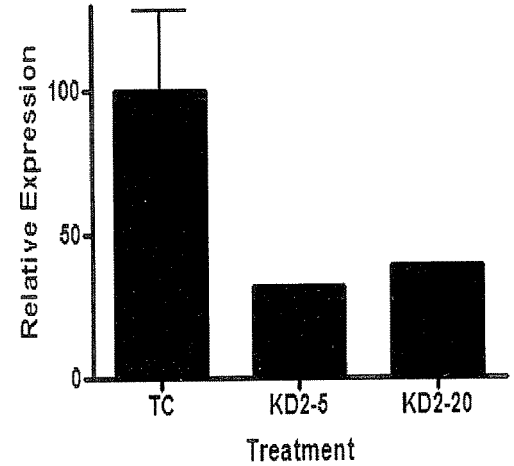
D
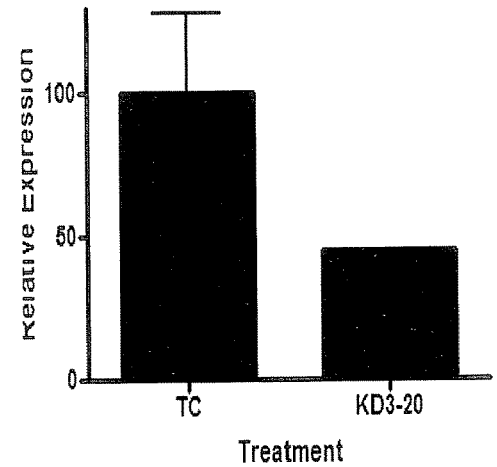

SEQUENCE LISTING

<160> NUMBER OF SEQ ID NOS: 97

<210> SEQ ID NO 1
<211> LENGTH: 21
<212> TYPE: DNA
<213> ORGANISM: Artificial
<220> FEATURE:
<223> OTHER INFORMATION: siRNA sequence

<400> SEQUENCE: 1
gccaaggtcc atgaggagat t                                              21

<210> SEQ ID NO 2
<211> LENGTH: 21
<212> TYPE: DNA
<213> ORGANISM: Artificial
<220> FEATURE:
<223> OTHER INFORMATION: siRNA sequence

<400> SEQUENCE: 2
gacaagggac agttgaagaa g                                              21

<210> SEQ ID NO 3
<211> LENGTH: 21
<212> TYPE: DNA
<213> ORGANISM: Artificial
<220> FEATURE:
<223> OTHER INFORMATION: siRNA sequence

<400> SEQUENCE: 3
cccaaagact tcaacccaaa g                                              21

<210> SEQ ID NO 4
<211> LENGTH: 21
<212> TYPE: DNA
<213> ORGANISM: Artificial
<220> FEATURE:
<223> OTHER INFORMATION: siRNA sequence

<400> SEQUENCE: 4
aagaacactg aggtgtaccc c                                              21

<210> SEQ ID NO 5
<211> LENGTH: 21
<212> TYPE: DNA
<213> ORGANISM: Artificial
<220> FEATURE:
<223> OTHER INFORMATION: siRNA sequence

<400> SEQUENCE: 5
aaggagattg atcaggtgat c                                              21

<210> SEQ ID NO 6
<211> LENGTH: 21
<212> TYPE: DNA
<213> ORGANISM: Artificial
<220> FEATURE:
<223> OTHER INFORMATION: siRNA sequence

<400> SEQUENCE: 6
caggaaagcg catttgtctt g                                              21

<210> SEQ ID NO 7
<211> LENGTH: 21
<212> TYPE: DNA

```
<213> ORGANISM: Artificial
<220> FEATURE:
<223> OTHER INFORMATION: siRNA sequence

<400> SEQUENCE: 7
gtgctccctg caatgtcatc t                                              21

<210> SEQ ID NO 8
<211> LENGTH: 21
<212> TYPE: DNA
<213> ORGANISM: Artificial
<220> FEATURE:
<223> OTHER INFORMATION: siRNA sequence

<400> SEQUENCE: 8
gtgctccttg caatgtcatc t                                              21

<210> SEQ ID NO 9
<211> LENGTH: 21
<212> TYPE: DNA
<213> ORGANISM: Artificial
<220> FEATURE:
<223> OTHER INFORMATION: siRNA sequence

<400> SEQUENCE: 9
gtgctccatg caatgtcatc t                                              21

<210> SEQ ID NO 10
<211> LENGTH: 21
<212> TYPE: DNA
<213> ORGANISM: Artificial
<220> FEATURE:
<223> OTHER INFORMATION: siRNA sequence

<400> SEQUENCE: 10
gtgctccctc caatgtgatc t                                              21

<210> SEQ ID NO 11
<211> LENGTH: 21
<212> TYPE: DNA
<213> ORGANISM: Artificial
<220> FEATURE:
<223> OTHER INFORMATION: siRNA sequence

<400> SEQUENCE: 11
gtgttccctg caatgtgatc t                                              21

<210> SEQ ID NO 12
<211> LENGTH: 21
<212> TYPE: DNA
<213> ORGANISM: Artificial
<220> FEATURE:
<223> OTHER INFORMATION: siRNA sequence

<400> SEQUENCE: 12
gtgctccctg caacgtgatc t                                              21

<210> SEQ ID NO 13
<211> LENGTH: 21
<212> TYPE: DNA
<213> ORGANISM: Artificial
<220> FEATURE:
<223> OTHER INFORMATION: siRNA sequence

<400> SEQUENCE: 13
tccagagatg gcagaccagg c                                              21
```

```
<210> SEQ ID NO 14
<211> LENGTH: 21
<212> TYPE: DNA
<213> ORGANISM: Artificial
<220> FEATURE:
<223> OTHER INFORMATION: siRNA sequence

<400> SEQUENCE: 14
atggagctct tcctcttctt c                                              21

<210> SEQ ID NO 15
<211> LENGTH: 21
<212> TYPE: DNA
<213> ORGANISM: Artificial
<220> FEATURE:
<223> OTHER INFORMATION: siRNA sequence

<400> SEQUENCE: 15
cctcttcttc acctgcctcc t                                              21

<210> SEQ ID NO 16
<211> LENGTH: 21
<212> TYPE: DNA
<213> ORGANISM: Artificial
<220> FEATURE:
<223> OTHER INFORMATION: siRNA sequence

<400> SEQUENCE: 16
cccagggcca ctttgtgaag c                                              21

<210> SEQ ID NO 17
<211> LENGTH: 21
<212> TYPE: DNA
<213> ORGANISM: Artificial
<220> FEATURE:
<223> OTHER INFORMATION: siRNA sequence

<400> SEQUENCE: 17
gacagtttaa gaagagagaa t                                              21

<210> SEQ ID NO 18
<211> LENGTH: 21
<212> TYPE: DNA
<213> ORGANISM: Artificial
<220> FEATURE:
<223> OTHER INFORMATION: siRNA sequence

<400> SEQUENCE: 18
gtttgtgaag aagtatggaa a                                              21

<210> SEQ ID NO 19
<211> LENGTH: 21
<212> TYPE: DNA
<213> ORGANISM: Artificial
<220> FEATURE:
<223> OTHER INFORMATION: siRNA sequence

<400> SEQUENCE: 19
cagtttgatt tagatgtgtc a                                              21

<210> SEQ ID NO 20
<211> LENGTH: 21
<212> TYPE: DNA
<213> ORGANISM: Artificial
<220> FEATURE:
<223> OTHER INFORMATION: siRNA sequence
```

```
<400> SEQUENCE: 20
catgccctac accaatgctg t                                              21

<210> SEQ ID NO 21
<211> LENGTH: 21
<212> TYPE: DNA
<213> ORGANISM: Artificial
<220> FEATURE:
<223> OTHER INFORMATION: siRNA sequence

<400> SEQUENCE: 21
ccaacctgaa aggttcagca a                                              21

<210> SEQ ID NO 22
<211> LENGTH: 21
<212> TYPE: DNA
<213> ORGANISM: Artificial
<220> FEATURE:
<223> OTHER INFORMATION: siRNA sequence

<400> SEQUENCE: 22
cctgaaaggt tcagcaagga g                                              21

<210> SEQ ID NO 23
<211> LENGTH: 21
<212> TYPE: DNA
<213> ORGANISM: Artificial
<220> FEATURE:
<223> OTHER INFORMATION: siRNA sequence

<400> SEQUENCE: 23
ggaactgcat tggcatgagg t                                              21

<210> SEQ ID NO 24
<211> LENGTH: 21
<212> TYPE: DNA
<213> ORGANISM: Artificial
<220> FEATURE:
<223> OTHER INFORMATION: siRNA sequence

<400> SEQUENCE: 24
cctttggaaa tggacccagg a                                              21

<210> SEQ ID NO 25
<211> LENGTH: 21
<212> TYPE: DNA
<213> ORGANISM: Artificial
<220> FEATURE:
<223> OTHER INFORMATION: siRNA sequence

<400> SEQUENCE: 25
ccaacagaga tgcagagagg a                                              21

<210> SEQ ID NO 26
<211> LENGTH: 21
<212> TYPE: DNA
<213> ORGANISM: Artificial
<220> FEATURE:
<223> OTHER INFORMATION: siRNA sequence

<400> SEQUENCE: 26
catgtgcatc aaggaggccc t                                              21

<210> SEQ ID NO 27
<211> LENGTH: 21
<212> TYPE: DNA
```

-continued

<213> ORGANISM: Artificial
<220> FEATURE:
<223> OTHER INFORMATION: siRNA sequence

<400> SEQUENCE: 27
gccaaatcca gaggtgtttg a                                              21

<210> SEQ ID NO 28
<211> LENGTH: 21
<212> TYPE: DNA
<213> ORGANISM: Artificial
<220> FEATURE:
<223> OTHER INFORMATION: siRNA sequence

<400> SEQUENCE: 28
aggaactgca taggacagac t                                              21

<210> SEQ ID NO 29
<211> LENGTH: 21
<212> TYPE: DNA
<213> ORGANISM: Artificial
<220> FEATURE:
<223> OTHER INFORMATION: siRNA sequence

<400> SEQUENCE: 29
ggcgctgact ctgctgcgct t                                              21

<210> SEQ ID NO 30
<211> LENGTH: 21
<212> TYPE: DNA
<213> ORGANISM: Artificial
<220> FEATURE:
<223> OTHER INFORMATION: siRNA sequence

<400> SEQUENCE: 30
ggacagcctg cagaaatgtg t                                              21

<210> SEQ ID NO 31
<211> LENGTH: 21
<212> TYPE: DNA
<213> ORGANISM: Artificial
<220> FEATURE:
<223> OTHER INFORMATION: siRNA sequence

<400> SEQUENCE: 31
ggacagcctt cagaaatgtg t                                              21

<210> SEQ ID NO 32
<211> LENGTH: 21
<212> TYPE: DNA
<213> ORGANISM: Artificial
<220> FEATURE:
<223> OTHER INFORMATION: siRNA sequence

<400> SEQUENCE: 32
aaggatgaag atggaaagga g                                              21

<210> SEQ ID NO 33
<211> LENGTH: 50
<212> TYPE: DNA
<213> ORGANISM: Mus musculus

<400> SEQUENCE: 33
tccaaaagga gattgatcag gtgatcggct cacaccggct accaactctt              50

<210> SEQ ID NO 34

```
<211> LENGTH: 50
<212> TYPE: DNA
<213> ORGANISM: Mus musculus

<400> SEQUENCE: 34
tccaaaagga gattgatcag gtgatcggct cacaccggct accaacccptt          50

<210> SEQ ID NO 35
<211> LENGTH: 50
<212> TYPE: DNA
<213> ORGANISM: Mus musculus

<400> SEQUENCE: 35
tccaaaagga gattgatcag gtgatcagtg cacaccatgt cccaacccptt          50

<210> SEQ ID NO 36
<211> LENGTH: 50
<212> TYPE: DNA
<213> ORGANISM: Mus musculus

<400> SEQUENCE: 36
tccaaaagga gattgatcag gtgatcggct cacaccggct accaacccptt          50

<210> SEQ ID NO 37
<211> LENGTH: 50
<212> TYPE: DNA
<213> ORGANISM: Mus musculus

<400> SEQUENCE: 37
tccaaaagga gattgatcag gtgatcggct cacaccggct accgactctt           50

<210> SEQ ID NO 38
<211> LENGTH: 50
<212> TYPE: DNA
<213> ORGANISM: Homo sapiens

<400> SEQUENCE: 38
tctacaggga gattgaacag gtgattggcc cacatcgccc tccagagctt           50

<210> SEQ ID NO 39
<211> LENGTH: 50
<212> TYPE: DNA
<213> ORGANISM: Mus musculus

<400> SEQUENCE: 39
acacactgtt ccgagggtac ctgctcccca agaacactga ggtgtacccc          50

<210> SEQ ID NO 40
<211> LENGTH: 50
<212> TYPE: DNA
<213> ORGANISM: Mus musculus

<400> SEQUENCE: 40
ataccatgtt ccgagggtac ctgctcccca agaacactga ggtgtacccc          50

<210> SEQ ID NO 41
<211> LENGTH: 50
<212> TYPE: DNA
<213> ORGANISM: Mus musculus

<400> SEQUENCE: 41
acacagtgtt ccgaggatac ctgctcccca agaacactga ggtgtacccc          50

<210> SEQ ID NO 42
```

```
<211> LENGTH: 50
<212> TYPE: DNA
<213> ORGANISM: Mus musculus

<400> SEQUENCE: 42
ataccatgtt ccgagggtac ctgctcccca agaacactga ggtgtacccc            50

<210> SEQ ID NO 43
<211> LENGTH: 50
<212> TYPE: DNA
<213> ORGANISM: Mus musculus

<400> SEQUENCE: 43
acacactgtt ccgaggatac ctgatcccca agaacactga ggtgtacccc            50

<210> SEQ ID NO 44
<211> LENGTH: 50
<212> TYPE: DNA
<213> ORGANISM: Homo sapiens

<400> SEQUENCE: 44
acaccagctt ccgagggtac atcatcccca aggacacaga agtatttctc            50

<210> SEQ ID NO 45
<211> LENGTH: 50
<212> TYPE: DNA
<213> ORGANISM: Mus musculus

<400> SEQUENCE: 45
aagcttttct gcccttctcc acaggaaagc gcatttgtct tggtgaaagc            50

<210> SEQ ID NO 46
<211> LENGTH: 50
<212> TYPE: DNA
<213> ORGANISM: Mus musculus

<400> SEQUENCE: 46
aagcttttct acccttctcc acaggaaagc gcatttgtct tggtgaaagc            50

<210> SEQ ID NO 47
<211> LENGTH: 50
<212> TYPE: DNA
<213> ORGANISM: Mus musculus

<400> SEQUENCE: 47
aagcttttct gcccttctcc acaggaaagc gcatttgtct tggcgaaggc            50

<210> SEQ ID NO 48
<211> LENGTH: 50
<212> TYPE: DNA
<213> ORGANISM: Mus musculus

<400> SEQUENCE: 48
aagcttttct gcccttctca acaggaaagc gcatttgtct tggtgaaagc            50

<210> SEQ ID NO 49
<211> LENGTH: 50
<212> TYPE: DNA
<213> ORGANISM: Mus musculus

<400> SEQUENCE: 49
aagctttcat gcccttctcc acaggaaagc gcatttgtct tggagaaggc            50

<210> SEQ ID NO 50
```

<211> LENGTH: 50
<212> TYPE: DNA
<213> ORGANISM: Homo sapiens

<400> SEQUENCE: 50
aagcttttat cccttctcc ttagggaagc ggatttgtct tggtgaaggc         50

<210> SEQ ID NO 51
<211> LENGTH: 63
<212> TYPE: DNA
<213> ORGANISM: Artificial
<220> FEATURE:
<223> OTHER INFORMATION: Synthetic oligonucleotide

<400> SEQUENCE: 51
gatccggaga ttgatcaggt gatcttcaag agagatcacc tgatcaatct ccttttttgg    60
aaa                                                                  63

<210> SEQ ID NO 52
<211> LENGTH: 63
<212> TYPE: DNA
<213> ORGANISM: Artificial
<220> FEATURE:
<223> OTHER INFORMATION: Synthetic oligonucleotide

<400> SEQUENCE: 52
gatccgaaca ctgaggtgta ccccttcaag agaggggtac acctcagtgt tctttttgg     60 aaa                                                                  63

<210> SEQ ID NO 53
<211> LENGTH: 76
<212> TYPE: DNA
<213> ORGANISM: Artificial
<220> FEATURE:
<223> OTHER INFORMATION: Synthetic oligonucleotide

<400> SEQUENCE: 53
ggatcccgca agacaaatgc gctttcctgt tgatatccgc aggaaagcgc atttgtcttg    60 tttttttccaa ctcgag                                                   76

<210> SEQ ID NO 54
<211> LENGTH: 75
<212> TYPE: DNA
<213> ORGANISM: Artificial
<220> FEATURE:
<223> OTHER INFORMATION: Synthetic oligonucleotide

<400> SEQUENCE: 54
ggatcccgac gattcgaggc gcagtgattt gatatccgat cactgctcct cgaatcgtct    60
tttttccaac tcgag                                                     75

<210> SEQ ID NO 55
<211> LENGTH: 76
<212> TYPE: DNA
<213> ORGANISM: Artificial
<220> FEATURE:
<223> OTHER INFORMATION: Synthetic oligonucleotide

<400> SEQUENCE: 55
ggatcccgct ttgggttgaa gtctttgggt tgatatccgc ccaaagactt caacccaaag    60 tttttttccaa ctcgag                                                   76

<210> SEQ ID NO 56

<211> LENGTH: 75
<212> TYPE: DNA
<213> ORGANISM: Artificial
<220> FEATURE:
<223> OTHER INFORMATION: Synthetic oligonucleotide

<400> SEQUENCE: 56
ggatcccaag gagattgatc aggtgatctt gatatccgga tcacctgatc aatctccttt    60
tttttccaac tcgag    75

<210> SEQ ID NO 57
<211> LENGTH: 75
<212> TYPE: DNA
<213> ORGANISM: Artificial
<220> FEATURE:
<223> OTHER INFORMATION: Synthetic oligonucleotide

<400> SEQUENCE: 57
ggatcccaag aacactgagg tgtaccccct tgatatccggg ggtacacctc agtgttcttt    60
tttttccaac tcgag    75

<210> SEQ ID NO 58
<211> LENGTH: 76
<212> TYPE: DNA
<213> ORGANISM: Artificial
<220> FEATURE:
<223> OTHER INFORMATION: Synthetic oligonucleotide

<400> SEQUENCE: 58
ggatcccgca agacaaatgc gctttcctgt tgatatccgc aggaaagcgc atttgtcttg    60 tttttttccaa ctcgag    76

<210> SEQ ID NO 59
<211> LENGTH: 79
<212> TYPE: DNA
<213> ORGANISM: Artificial
<220> FEATURE:
<223> OTHER INFORMATION: Synthetic oligonucleotide

<400> SEQUENCE: 59
ggatcccgcc tggtctgcca tctctggatt gatatccgtc cgtccagaga tggcagacca    60
ggcttttttc caactcgag    79

<210> SEQ ID NO 60
<211> LENGTH: 76
<212> TYPE: DNA
<213> ORGANISM: Artificial
<220> FEATURE:
<223> OTHER INFORMATION: Synthetic oligonucleotide

<400> SEQUENCE: 60
ggatcccgcc tcttcttcac ctgcctcctt tgatatccga ggaggcaggt gaagaagagg    60 tttttttccaa ctcgag    76

<210> SEQ ID NO 61
<211> LENGTH: 75
<212> TYPE: DNA
<213> ORGANISM: Artificial
<220> FEATURE:
<223> OTHER INFORMATION: Synthetic oligonucleotide

<400> SEQUENCE: 61
ggatcccagg gcctccttga tgcacatgtt gatatccgca tgtgcatcaa ggaggccctt    60

```
tttttccaac tcgag                                                   75

<210> SEQ ID NO 62
<211> LENGTH: 76
<212> TYPE: DNA
<213> ORGANISM: Artificial
<220> FEATURE:
<223> OTHER INFORMATION: Synthetic oligonucleotide

<400> SEQUENCE: 62
ggatcccgcc aacagagatg cagagaggat tgatatccgt cctctctgca tctctgttgg   60 tttttttccaa ctcgag                                                 76

<210> SEQ ID NO 63
<211> LENGTH: 15
<212> TYPE: PRT
<213> ORGANISM: Artificial
<220> FEATURE:
<223> OTHER INFORMATION: Cyp2b antigenic peptide

<400> SEQUENCE: 63

Leu His Asp Pro Gln Tyr Phe Glu Gln Pro Asp Ser Phe Asn Cys
1               5                   10                  15

<210> SEQ ID NO 64
<211> LENGTH: 20
<212> TYPE: DNA
<213> ORGANISM: Artificial
<220> FEATURE:
<223> OTHER INFORMATION: Q-PCR primer

<400> SEQUENCE: 64
agcaggctac cttcgactgg                                              20

<210> SEQ ID NO 65
<211> LENGTH: 20
<212> TYPE: DNA
<213> ORGANISM: Artificial
<220> FEATURE:
<223> OTHER INFORMATION: Q-PCR primer

<400> SEQUENCE: 65
gctgctgaag gctatgccat                                              20

<210> SEQ ID NO 66
<211> LENGTH: 19
<212> TYPE: DNA
<213> ORGANISM: Artificial
<220> FEATURE:
<223> OTHER INFORMATION: Q-PCR primer

<400> SEQUENCE: 66
ctgagaccac aagcgccac                                               19

<210> SEQ ID NO 67
<211> LENGTH: 21
<212> TYPE: DNA
<213> ORGANISM: Artificial
<220> FEATURE:
<223> OTHER INFORMATION: Q-PCR primer

<400> SEQUENCE: 67
cttgaccatg agcaggactc c                                            21

<210> SEQ ID NO 68
<211> LENGTH: 22
```

<212> TYPE: DNA
<213> ORGANISM: Artificial
<220> FEATURE:
<223> OTHER INFORMATION: Q-PCR primer

<400> SEQUENCE: 68
ctgaatccgc tcctccacac tc                                        22

<210> SEQ ID NO 69
<211> LENGTH: 22
<212> TYPE: DNA
<213> ORGANISM: Artificial
<220> FEATURE:
<223> OTHER INFORMATION: Q-PCR primer

<400> SEQUENCE: 69
tgagccaacc ttcaaggaat at                                        22

<210> SEQ ID NO 70
<211> LENGTH: 26
<212> TYPE: DNA
<213> ORGANISM: Artificial
<220> FEATURE:
<223> OTHER INFORMATION: Q-PCR primer

<400> SEQUENCE: 70
gaactgagac taccagcacc actcct                                    26

<210> SEQ ID NO 71
<211> LENGTH: 22
<212> TYPE: DNA
<213> ORGANISM: Artificial
<220> FEATURE:
<223> OTHER INFORMATION: Q-PCR primer

<400> SEQUENCE: 71
tgagcatgag caggaaacca ct                                        22

<210> SEQ ID NO 72
<211> LENGTH: 21
<212> TYPE: DNA
<213> ORGANISM: Artificial
<220> FEATURE:
<223> OTHER INFORMATION: Q-PCR primer

<400> SEQUENCE: 72
ggcctcaaag ccctactgtc a                                         21

<210> SEQ ID NO 73
<211> LENGTH: 19
<212> TYPE: DNA
<213> ORGANISM: Artificial
<220> FEATURE:
<223> OTHER INFORMATION: Q-PCR primer

<400> SEQUENCE: 73
aacgccaaaa cctttaatc                                            19

<210> SEQ ID NO 74
<211> LENGTH: 20
<212> TYPE: DNA
<213> ORGANISM: Artificial
<220> FEATURE:
<223> OTHER INFORMATION: Q-PCR primer

<400> SEQUENCE: 74
atactctata tttgggcagg                                           20

<210> SEQ ID NO 75
<211> LENGTH: 18
<212> TYPE: DNA
<213> ORGANISM: Artificial
<220> FEATURE:
<223> OTHER INFORMATION: Q-PCR primer

<400> SEQUENCE: 75
gttcctccac aaggcaac                                                    18

<210> SEQ ID NO 76
<211> LENGTH: 21
<212> TYPE: DNA
<213> ORGANISM: Artificial
<220> FEATURE:
<223> OTHER INFORMATION: Q-PCR primer

<400> SEQUENCE: 76
cattgaacac tggcaacatt g                                                21

<210> SEQ ID NO 77
<211> LENGTH: 21
<212> TYPE: DNA
<213> ORGANISM: Artificial
<220> FEATURE:
<223> OTHER INFORMATION: Q-PCR primer

<400> SEQUENCE: 77
gtcacaggtt acttcatgca c                                                21

<210> SEQ ID NO 78
<211> LENGTH: 21
<212> TYPE: DNA
<213> ORGANISM: Artificial
<220> FEATURE:
<223> OTHER INFORMATION: Q-PCR primer

<400> SEQUENCE: 78
ctttccttca ccctgcattc c                                                21

<210> SEQ ID NO 79
<211> LENGTH: 24
<212> TYPE: DNA
<213> ORGANISM: Artificial
<220> FEATURE:
<223> OTHER INFORMATION: Q-PCR primer

<400> SEQUENCE: 79
ctcatcctgc agtttttttct ggat                                            24

<210> SEQ ID NO 80
<211> LENGTH: 20
<212> TYPE: DNA
<213> ORGANISM: Artificial
<220> FEATURE:
<223> OTHER INFORMATION: Q-PCR primer

<400> SEQUENCE: 80
cacatcattt ggcgtgaacg                                                  20

<210> SEQ ID NO 81
<211> LENGTH: 21
<212> TYPE: DNA
<213> ORGANISM: Artificial
<220> FEATURE:
<223> OTHER INFORMATION: Q-PCR primer

```
<400> SEQUENCE: 81
tttctgcaca aagggatcct g                                      21

<210> SEQ ID NO 82
<211> LENGTH: 21
<212> TYPE: DNA
<213> ORGANISM: Artificial
<220> FEATURE:
<223> OTHER INFORMATION: Q-PCR primer

<400> SEQUENCE: 82
gtggagaaag ccaaagggat t                                      21

<210> SEQ ID NO 83
<211> LENGTH: 25
<212> TYPE: DNA
<213> ORGANISM: Artificial
<220> FEATURE:
<223> OTHER INFORMATION: Q-PCR primer

<400> SEQUENCE: 83
gaagaccaaa ggatcaaaaa agtca                                  25

<210> SEQ ID NO 84
<211> LENGTH: 23
<212> TYPE: DNA
<213> ORGANISM: Artificial
<220> FEATURE:
<223> OTHER INFORMATION: Q-PCR primer

<400> SEQUENCE: 84
ttgtggagga agccaaaaag ttt                                    23

<210> SEQ ID NO 85
<211> LENGTH: 23
<212> TYPE: DNA
<213> ORGANISM: Artificial
<220> FEATURE:
<223> OTHER INFORMATION: Q-PCR primer

<400> SEQUENCE: 85
ttgtggagga agccaaaaag ttt                                    23

<210> SEQ ID NO 86
<211> LENGTH: 20
<212> TYPE: DNA
<213> ORGANISM: Artificial
<220> FEATURE:
<223> OTHER INFORMATION: Q-PCR primer

<400> SEQUENCE: 86
atggccgttc ttagttggtg                                        20

<210> SEQ ID NO 87
<211> LENGTH: 20
<212> TYPE: DNA
<213> ORGANISM: Artificial
<220> FEATURE:
<223> OTHER INFORMATION: Q-PCR primer

<400> SEQUENCE: 87
atgccagagt ctcgttcgtt                                        20

<210> SEQ ID NO 88
<211> LENGTH: 21
```

```
<212> TYPE: DNA
<213> ORGANISM: Artificial
<220> FEATURE:
<223> OTHER INFORMATION: Q-PCR primer

<400> SEQUENCE: 88
gctatgttgc tctagacttc g                                              21

<210> SEQ ID NO 89
<211> LENGTH: 18
<212> TYPE: DNA
<213> ORGANISM: Artificial
<220> FEATURE:
<223> OTHER INFORMATION: Q-PCR primer

<400> SEQUENCE: 89
cctcatggtg ctaggagc                                                  18

<210> SEQ ID NO 90
<211> LENGTH: 20
<212> TYPE: DNA
<213> ORGANISM: Artificial
<220> FEATURE:
<223> OTHER INFORMATION: pRNAT-specific screening primer

<400> SEQUENCE: 90
ggatcccaag aacactgagg                                                20

<210> SEQ ID NO 91
<211> LENGTH: 20
<212> TYPE: DNA
<213> ORGANISM: Artificial
<220> FEATURE:
<223> OTHER INFORMATION: pRNAT-specific screening primer

<400> SEQUENCE: 91
ttatgtaacg cggaactcca                                                20

<210> SEQ ID NO 92
<211> LENGTH: 20
<212> TYPE: DNA
<213> ORGANISM: Artificial
<220> FEATURE:
<223> OTHER INFORMATION: pSilencer-specific screening primer

<400> SEQUENCE: 92
ttgtacaccc taagcctccg                                                20

<210> SEQ ID NO 93
<211> LENGTH: 21
<212> TYPE: DNA
<213> ORGANISM: Artificial
<220> FEATURE:
<223> OTHER INFORMATION: pSilencer-specific screening primer

<400> SEQUENCE: 93
gggtttatat atcttgtgga a                                              21

<210> SEQ ID NO 94
<211> LENGTH: 20
<212> TYPE: DNA
<213> ORGANISM: Artificial
<220> FEATURE:
<223> OTHER INFORMATION: Q-PCR primer

<400> SEQUENCE: 94
gagggcctat ttcccatgat                                                20
```

```
<210> SEQ ID NO 95
<211> LENGTH: 20
<212> TYPE: DNA
<213> ORGANISM: Artificial
<220> FEATURE:
<223> OTHER INFORMATION: Q-PCR primer

<400> SEQUENCE: 95
tcaaggggta cacctcagtg                                               20

<210> SEQ ID NO 96
<211> LENGTH: 19
<212> TYPE: DNA
<213> ORGANISM: Artificial
<220> FEATURE:
<223> OTHER INFORMATION: Q-PCR primer

<400> SEQUENCE: 96
agggcctatt tcccatgat                                                19

<210> SEQ ID NO 97
<211> LENGTH: 19
<212> TYPE: DNA
<213> ORGANISM: Artificial
<220> FEATURE:
<223> OTHER INFORMATION: Q-PCR primer

<400> SEQUENCE: 97
aaatcactgc gcctcgaat                                                19
```

METHODS OF INHIBITING MULTIPLE CYTOCHROME P450 GENES WITH SIRNA

CROSS REFERENCE TO RELATED APPLICATIONS

This application claims the benefit, under 35 U.S.C. §119 (e), of U.S. Provisional Application Ser. No. 61/046,937, filed Apr. 22, 2008, the disclosure of which is incorporated herein by reference in its entirety.

STATEMENT OF GOVERNMENT SUPPORT

Research related to this invention was supported, at least in part, by U.S. Government Grant No. GM008012 awarded by the NIH. The U.S. Government has certain rights in this invention.

FIELD OF THE INVENTION

The present invention relates to siRNAs that are targeted to RNAs encoding two or more enzymes of a subfamily of cytochrome P450 (CYP) enzymes, along with vectors, cells, and kits comprising the siRNAs. The invention further relates to methods of decreasing expression of two or more CYP subfamily genes in a non-human animal, an animal in which expression of two or more CYP subfamily genes has been decreased, and methods of using such animals to study the function and/or activity of cytochrome P450 enzymes.

BACKGROUND OF THE INVENTION

Cytochrome P450 enzymes (CYPs) are critical members of an organism's detoxification systems that help metabolize and eliminate endogenous and exogenous toxic chemicals. The CYPs are phase I enzymes that mono-oxygenate, reduce, and hydrolyze various substrates, yielding more polar, water-soluble metabolites that can be conjugated by phase II enzymes and removed rapidly. The CYPs are also involved in the formation of toxic intermediates and may cause adverse drug reactions (ADRs). It is estimated that between 635,000 and 770,000 patients have a serious adverse drug reaction each year and approximately 106,000 people die from ADRs in the United States (Lazarou et al, *J. Am. Med. Assoc.* 279: 1200 (1998)). This would make ADRs between the $4^{th}$ and $6^{th}$ leading cause of death in the United States. Recent research suggests that pharmacogenetic data on CYP polymorphisms will ultimately explain nearly 20% of ADRs. In addition, nearly 50% of ADRs can be explained by physiological or environmental factors, which includes the induction of CYPs (Ingelman-Sundberg et al., *J. Inter, Med.* 250:186 (2001)).

CYPs are grouped into families, subfamilies and isoforms. The human CYP genes have been arranged into 18 families, 43 subfamilies, and 57 isoforms; the mouse CYP genes have been arranged into 13 families, 43 subfamilies, and 102 isoforms (Nelson et al., *Pharmacogenetics* 14:1 (2004)). For example, with Cyp3a4, CYP=cytochrome P450, 3=the family, a=the subfamily, and 4 is the isoform. It is the CYPs in families 1-4 that contribute most to the metabolism of xenobiotics, including chemical contaminants and pharmaceuticals (Waxman, *Arch Biochem Biophys.* 369:11 (1999)). In humans, CYPs such as CYP3A4, CYP2D6, CYP2B6, CYP2C9, and CYP1A2 are very important in xenobiotic metabolism, as well as steroid catabolism, bile acid metabolism, bilirubin elimination, etc. In mice, CYPs such as Cyp3a11, Cyp3a25, Cyp3a41, Cyp2b9, Cyp2b10, Cyp2d9, Cyp2d22, Cyp2c29, Cyp2c37, and Cyp2c40 have similar activities.

The constitutive androstane receptor (CAR) and its cousin, pregnane X receptor (PXR) are relatively new members of the nuclear receptor family that dimerize with retinoid X receptor-α following activation by xenobiotics and endobiotics and in turn act as master regulators of phases I through III enzymes involved in the detoxification and elimination of steroids, bile acids, and xenobiotics. Cyp2b enzymes are inducible by both CAR and PXR, but the Cyp2b enzymes are of special interest with regard to CAR because of the identification of phenobarbital response elements in the 5' regions of Cyp2b genes and the elucidation of CAR as the receptor that is activated following phenobarbital exposure. Several CAR activators such as phenobarbital, 1,4-bis[2-(3,5-dichloropyridyloxy)]benzene (TCPOBOP), phenyloin, nonylphenol, and O-(3,4-dichlorobenzyl)oxime (CITCO) are potent Cyp2b inducers and therefore Cyp2b is an excellent biomarker for CAR activation.

There are more P450 isoforms in each subfamily of the mouse genome than there are in the human genome. For example, in humans there are three members of the Cyp2a subfamily, one member of the Cyp2b subfamily, four members of the Cyp2c subfamily, one member of the Cyp2d subfamily, and four members of the Cyp3a subfamily for a total of 13 isoforms in these subfamilies. In mice, there are four members of the Cyp2a subfamily, five members of the Cyp2b subfamily, 15 members of the Cyp2c subfamily, nine members of the Cyp2d subfamily, and eight members of the Cyp3a subfamily for a total of 41 isoforms in these subfamilies. Table 1 shows the corresponding mouse and human isoforms in each of the principle subfamilies involved in detoxification.

TABLE 1

Human and mouse CYP genes involved in detoxification.

| Human | Mouse |
|---|---|
| CYP1A1, 1A2 | Cyp1a1*, 1a2* |
| CYP1B1 | Cyp1b1* |
| CYP2A6, 2A7, 2A13 | Cyp2a4, 2a5, 2a12, 2a22 |
| CYP2B6 | Cyp2b9, 2b10, 2b13, 2b19, 2b23 |
| CYP2C8, 2C9, 2C18, 2C19 | Cyp2c29, 2c37, 2c38, 2c39, 2c40, 2c44, 2c50, 2c54, 2c55, 2c65, 2c66, 2c67, 2c68, 2c69, 2c70 |
| CYP2D6 | Cyp2d9, 2d10, 2d11, 2d12, 2d13, 2d22, 2d26, 2d34, 2d40 |
| CYP2E1 | Cyp2e1* |

TABLE 1-continued

Human and mouse CYP genes involved in detoxification.

| Human | Mouse |
|---|---|
| CYP3A4, 3A5, 3A7, 3A43 | Cyp3a11, 3a13, 3a16, 3a25, 3a41, 3a44, 3a57, 3a59# |
| CYP4A11, 4A22 | Cyp4a10, 4a12, 4a14, 4a29, 4a30, 4a31, 4a32 |
| CYP4F2, 4F3, 4F8, 4F11, 4F12, 4F22 | Cyp4f13, 4f14, 4f15, 4f16, 4f17, 4f18, 4f37, 4f39, 4f40 |

*genes for which knockout mice have been produced
The Cyp3a subfamily was recently knocked out by deleting a portion of a chromosome that contained the genes in a tandem repeat region (van Herwaarden et al., J. Clin. Invest. 117: 3583 (2007)).

This redundancy has made typical P450 gene "knockouts" impractical as other subfamily members are available to metabolize a compound of interest. Knocking out Cyp2b10, for example, would have little effect on the physiology of the mouse since Cyp2b9, Cyp2b13, Cyp2b19, and Cyp2b23. are still available to metabolize the compound. Furthermore, the cost of making a pentuplet Cyp2b knockout is prohibitively expensive. Therefore useful knockouts of P450 members have been rare. There are currently six genes knocked out of the 102 mouse members and one subfamily; two involved in bile acid homeostasis (Cyp7a1, Cyp26a1) and four detoxification genes (Cyp1a1, Cyp1a2, Cyp2e1, Cyp1b1, indicated with an asterisk in Table 1 and recently a chromosomal deletion of the CYP3A subfamily where all the members are found in a tandem repeat). This means that there are few P450-null mice for the P450s critical in xenobiotic detoxification. Further, there are almost no P450-null mice for the constitutively expressed xenobiotic detoxifying P450s in the Cyp2-4 families that are also critical in steroid hormone homeostasis, fatty acid metabolism, and bile acid metabolism. Therefore, the exact physiological roles these different CYP families play in vivo in detoxification, steroid hormone homeostasis, and bile acid elimination has not been thoroughly studied using proven, substantiated techniques.

RNA interference (RNAi) technologies have been developed that allow for the "knockdown" of genes. Small interfering RNAs (siRNAs) are short, double-stranded RNA molecules that comprise sequences complementary to mRNAs, and in turn target the mRNA for degradation by hybridizing with the mRNA to form a double stranded RNA (dsRNA) molecule. (Elbashir et al., *Genes Dev.* 15:188 (2001); Brummelkamp et al., *Science* 296:550 (2002)). RNAi was first described in *Caenorhabditis elegans*, when it was discovered that homologous dsRNA resulted in the post-transcriptional silencing of a specific gene (Fire et al., *Nature* 391:806 (1998)). The gene silencing effect of dsRNA is mediated in a two-step process: 1) the dsRNA is recognized by Dicer, a member of a RNase III family of nucleases, that processes the dsRNA into small double-stranded molecules called siRNAs. 2) The siRNAs are bound by a protein complex called RISC (RNA-induced silencing complex) that contains RNase activity and targets the mRNA for degradation. Typically, siRNA or short hairpin RNA (shRNA) sense and antisense strands are only 21 nucleotides in length because longer dsRNA also elicits an anti-viral interferon response. This results in cessation of all protein synthesis, not just that of the homologous, specific target strand.

The present invention addresses previous shortcomings in the art by providing compositions and methods for the knockdown of multiple members of a P450 subfamily by targeting common mRNA sequences.

SUMMARY OF THE INVENTION

The present invention relates to siRNAs targeted to RNAs encoding two or more enzymes of a subfamily of cytochrome P450 enzymes, e.g., three or more, four or more, five or more, or all of the known members. In one embodiment, the CYP subfamily is selected from the group consisting of Cyp2a, Cyp2b, Cyp2c, Cyp2d, Cyp2j, Cyp3a, Cyp4a, and Cyp4f. In one embodiment, the siRNAs are at least 70% identical to one of SEQ ID NOS:1 to 32 or a fragment thereof of at least ten contiguous nucleotides.

Another aspect of the invention relates to vectors comprising polynucleotides encoding one or more siRNAs of the invention. The vectors may comprise a promoter operably linked to the polynucleotides encoding the siRNA. In one embodiment, the vectors encode a shRNA (a single stranded RNA comprising two complementary sequences that folds into a double stranded region and a loop (e.g., a hairpin)) that is processed after expression into a siRNA (e.g., by cleavage of the loop).

A further aspect of the invention relates to cells comprising one or more siRNAs of the invention and/or one or more vectors of the invention.

Another aspect of the invention is a kit comprising one or more siRNAs, vectors, and/or cells of the invention or any combination thereof.

The invention further relates to methods of decreasing expression of two or more genes from a CYP subfamily in a non-human animal, comprising delivering to a cell of said animal one or more of the siRNAs of the invention. In one embodiment, the animal is a mouse. In another embodiment, expression of the two or more genes from a CYP subfamily is decreased by at least about 50%.

An additional aspect of the invention relates to a non-human animal in which expression of two or more genes from a CYP subfamily has been decreased by delivery of the siRNAs of the invention to a cell of the animal. In one embodiment, the animal is a mouse. In another embodiment, the siRNAs are delivered to the animal in the form of a vector encoding the siRNAs or a precursor of the siRNAs (e.g., a shRNA or dsRNA). In a further embodiment, expression of the two or more genes from a CYP subfamily is decreased by at least about 50%. In one embodiment, the non-human animal further comprises at least one polynucleotide encoding a human CYP enzyme.

Another aspect of the invention relates to methods for studying the function of an enzyme of a CYP subfamily of cytochrome P450 enzymes in a non-human animal, comprising decreasing the expression of two or more genes from a CYP subfamily in the animal by delivering a siRNA of the invention to a cell of the animal, and comparing the phenotype of the animal to the phenotype of a control animal.

A further aspect of the invention relates to methods for determining the role of an enzyme of a CYP subfamily of cytochrome P450 enzymes in the metabolism, elimination, and/or homeostasis of a compound in a non-human animal, comprising delivering the compound to an animal in which the expression of two or more genes from a CYP subfamily has been decreased by delivery of a siRNA of the invention to a cell of the animal, and comparing the metabolism, elimination, and/or homeostasis of the compound to the metabolism, elimination, and/or homeostasis of the compound after delivery to a control animal. In one embodiment, the compound is an endobiotic or a xenobiotic.

One aspect of the invention relates to methods for studying the function of an exogenous human enzyme of a CYP subfamily of cytochrome P450 enzymes in a non-human animal, comprising expressing a human CYP subfamily gene in an animal in which the expression of two or more genes from a CYP subfamily of the non-human animal has been decreased by delivery of a siRNA of the invention to a cell of the animal, and comparing the phenotype of the animal to the phenotype of a control animal.

A further aspect of the invention relates to methods for studying the function of an exogenous human polymorphic variant enzyme of a CYP subfamily of cytochrome P450 enzymes in a non-human animal, comprising expressing a human polymorphic variant CYP subfamily gene in an animal in which the expression of two or more genes from a CYP subfamily of the non-human animal has been decreased by delivery of a siRNA of the invention to a cell of the animal, and comparing the phenotype of the animal to the phenotype of a control animal.

An additional aspect of the invention relates to methods for identifying a siRNA that decreases the expression of two or more genes in a multi-gene family, comprising comparing the nucleotide sequence of two or more genes in the multi-gene family to each other, identifying a segment of at least about 12 contiguous nucleotides that is at least about 70% identical in each of the genes, and preparing a siRNA specific for the identified segment. In one embodiment, the methods further comprise the step of testing the siRNA to determine if it decreases expression of two or more genes in a multi-gene family in assays as described herein and as known in the art.

The present invention is explained in greater detail in the drawings herein and the specification set forth below.

BRIEF DESCRIPTION OF THE DRAWINGS

FIG. 1 shows three siRNA target areas KD1, KD2, and KD3 (shaded areas) of the Cyp2b genes (SEQ ID NOS:33-50). Homologous positions between the mouse genes and the human gene are indicated with asterisks.

FIGS. 3A-3C show the reduction of expression of Cyp2b9 and Cyp2b10 by RNAi constructs. TCPOBOP (TC)-induced primary mouse hepatocytes were transduced with the Cyp2b-KD2 and KD3 lentivirus constructs. FIGS. 3A and 3B show the relative expression of Cyp2b9 in TC-treated hepatocytes transduced with KD2 (5 and 20 MOI) (3A) or KD3 (3B). FIGS. 3C and 3D show the relative expression of Cyp2b10 in TC-treated hepatocytes transduced with KD2 (5 and 20 MOI) (3C) or KD3 (20 MOI) (3D). Expression of Cyp2b9 and Cyp2b10 was compared to TC treated cells transduced with a scrambled lentivirus. Both constructs reduced the expression of Cyp2b9, but only KD2 reduced the expression of Cyp2b10.

DETAILED DESCRIPTION OF THE INVENTION

Definitions

Figures 2A, 2B, 2C:
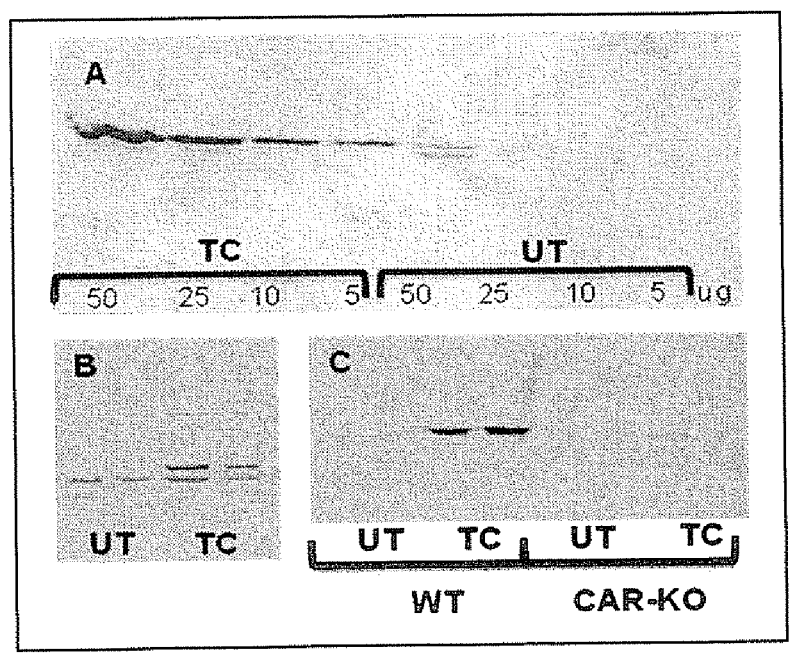
FIGS. 2A-2C show the binding affinity and specificity of the Cyp2b antibody. (A) Western blot using antibody showing Cyp2b levels at several different microsome concentrations in TCPOBOP-treated and untreated mouse microsomes. (B) Western blot using Gentest antibody against microsomes (100 μg protein) from untreated and TCPOBOP-treated mouse liver. The lower band is Cyp2a and the upper band is Cyp2b. (C) Western blot using Cyp2b10 antibody from Dr. Randy Rose against mouse liver microsomes (100 μg protein).

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to a siRNA sequence of this invention, means a siRNA that consists of both the recited sequence (e.g., SEQ ID NO) and a total of ten or less (e.g., 1, 2, 3, 4, 5, 6, 7, 8, 9, or 10) additional nucleotides on the 5' and/or 3' ends of the recited sequence such that the ability of the siRNA to bind to its target mRNA is not materially altered. The total of ten or less additional nucleotides includes the total number of additional nucleotides on both the 5' and 3' ends added together. The term "materially altered," as applied to siRNA binding, refers to an increase or decrease in binding affinity of at least about 50% or more as compared to the binding affinity of a siRNA consisting of the recited sequence.

As used herein, "nucleic acid," "nucleotide sequence" and "polynucleotide" encompass both RNA and DNA, including cDNA, genomic DNA, mRNA, synthetic (e.g., chemically synthesized) DNA and chimeras of RNA and DNA. The term polynucleotide or nucleotide sequence refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid or nucleotide sequence of this invention.

An "isolated nucleic acid" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

An isolated cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment" will be understood to mean a nucleotide sequence of reduced length relative to a reference nucleic acid or nucleotide sequence and comprising, consisting essentially of and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially or and/or consist of, oligonucleotides having a length of at least about 6, 7, 8, 9, 10, 11, 12, 13, 14, 15, 16, 17, 18, 19, 20, 21, 22, 23, 24, or 25 consecutive nucleotides of a nucleic acid or nucleotide sequence according to the invention.

Several methods known in the art may be used to produce a polynucleotide and/or vector construct according to this invention. As described herein, a vector of this invention can include, but is not limited to, any of the following vectors and/or their derivatives: human or animal viruses such as lentivirus, vaccinia virus or adenovirus; insect viruses such as baculovirus; yeast vectors; bacteriophage vectors (e.g., lambda), and plasmid and cosmid vectors, to name but a few.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral nucleic acid molecules for introducing a nucleic acid into a cell in vitro, ex vivo, and/or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript® vector. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Felgner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell. A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or in an activity or function of the cell. The transforming nucleic acid can be integrated (covalently linked) into chromosomal DNA making up the genome of the cell or it can be present as a stable plasmid.

"Promoter" refers to a nucleic acid sequence capable of controlling the expression of a coding sequence or functional RNA. In general, a coding sequence is located 3' to a promoter sequence. Promoters may be derived in their entirety from a native sequence, or be composed of different elements derived from different promoters found in nature, or even comprise synthetic nucleic acid segments. It is understood by those skilled in the art that different promoters may direct the expression of a nucleotide sequence in different tissues or cell types, or at different stages of development, or in response to different environmental or physiological conditions. Promoters that cause a nucleotide sequence to be expressed in most cell types at most times are commonly referred to as "constitutive promoters." Promoters that cause a nucleotide sequence to be expressed in a specific cell type are commonly referred to as "cell-specific promoters" or "tissue-specific promoters." Promoters that cause a nucleotide sequence to be expressed at a specific stage of development or cell differentiation are commonly referred to as "developmentally-specific promoters" or "cell differentiation-specific promoters." Promoters that are induced and cause a nucleotide sequence to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, nucleotide sequences of different lengths may have identical promoter activity.

A "promoter sequence" is a nucleic acid regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence can be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are nucleic acid regulatory sequences, such as promoters, enhancers, terminators, and the like, that provide for the expression of a coding sequence in a cell. For example, in eukaryotic cells, polyadenylation signals are control sequences.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense and/or antisense orientation.

The plasmids or vectors may further comprise at least one promoter suitable for driving expression of a nucleotide sequence in a cell. The term "expression vector" means a vector, plasmid or vehicle designed to enable the expression of an inserted nucleotide sequence following delivery of a nucleotide sequence into a cell. The cloned nucleotide sequence, i.e., the inserted nucleotide sequence, is usually placed under the control of control elements such as a promoter, a minimal promoter, an enhancer, or the like. Initiation control regions or promoters, which are useful to drive expression of a nucleic acid in a cell are numerous and familiar to those skilled in the art. Virtually any promoter capable of driving expression of a nucleotide sequence is suitable for the present invention, including but not limited to: viral promoters, bacterial promoters, animal promoters, mammalian promoters, synthetic promoters, constitutive promoters, tissue specific promoters, developmental specific promoters, inducible promoters, and/or light regulated promoters.

Non-limiting examples of promoters of this invention include CYC1, HIS3, GAL1, GAL4, GAL10, ADH1, PGK, PHO5, GAPDH, ADC1, TRP1, URA3, LEU2, ENO, U6, H1, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-promoters, cauliflower mosaic virus 35S, CMV 35S minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis and/or disease-related promoters, and promoters that exhibit tissue specificity, such as the elastase I gene control region, which is active in pancreatic acinar cells; the insulin gene control region active in pancreatic beta cells, the immunoglobulin gene control region active in lymphoid cells, the mouse mammary tumor virus control region active in testicular, breast, lymphoid and mast cells; the albumin gene promoter, the Apo AI and Apo AII control regions active in liver, the alpha-fetoprotein gene control region active in liver, the alpha 1-antitrypsin gene control region active in the liver, the beta-globin gene control region active in myeloid cells, the myelin basic protein gene control region active in oligodendrocyte cells in the brain, the myosin light chain-2 gene control region active in skeletal muscle, and the gonadotropic releasing hormone gene control region active in the hypothalamus, the pyruvate kinase promoter, the villin promoter, the promoter of the fatty acid binding intestinal protein, the promoter of smooth muscle cell α-actin, and the like. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to nucleic acid sequences located downstream (3') of a coding sequence and may comprise polyadenylation [poly(A)] recognition sequences and other sequences encoding regulatory signals capable of affecting mRNA processing or nucleic acid expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

The term "percent identity," as known in the art, describes a relationship between two or more polypeptide sequences or two or more polynucleotide sequences, as determined by comparing the sequences. In the art, "identity" also means the degree of sequence relatedness between polypeptide or polynucleotide sequences as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

Exemplary methods to determine identity are designed to give the best match between the sequences tested. Methods to determine identity and similarity are codified in publicly available computer programs. Sequence alignments and percent identity calculations can be performed using the Megalign program of the LASERGENE bioinformatics computing suite (DNASTAR Inc., Madison, Wis.). Multiple alignment of the sequences may be performed using the Clustal method of alignment (Higgins and Sharp (1989) CABIOS. 5:151-153) with the default parameters (GAP PENALTY=10, GAP LENGTH PENALTY=10). Exemplary default parameters for pairwise alignments using the Clustal method can be selected: KTUPLE 1, GAP PENALTY=3, WINDOW=5 and DIAGONALS SAVED=5.

The term "sequence analysis software" refers to any computer algorithm or software program that is useful for the analysis of nucleotide and/or amino acid sequences. "Sequence analysis software" is commercially available or can be independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., J. Mol. Biol. 215:403-410 (1990), and DNASTAR (DNASTAR, Inc. 1228 S. Park St. Madison, Wis. 53715 USA). Within the context of this application it will be understood that where sequence analysis software is used for analysis, the results of the analysis will be based on the "default values" of the program referenced, unless otherwise specified. As used herein "default values" will mean any set of values or parameters, which originally load with the software when first initialized.

The term "therapeutically effective amount" or "effective amount," as used herein, refers to that amount of a composition of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art.

"Pharmaceutically acceptable," as used herein, means a material that is not biologically or otherwise undesirable, i.e., the material may be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; latest edition). Exemplary pharmaceutically acceptable carriers for the compositions of this invention include, but are not limited to, sterile pyrogen-free water and sterile pyrogen-free physiological saline solution.

The term "siRNA," as used herein, refers to a double-stranded RNA molecule that binds to a mRNA to which it is targeted and inhibits translation of the mRNA into a protein encoded by that mRNA. The term includes the siRNA itself as well as precursors of the siRNA, such as double-stranded shRNA molecules comprising a loop that is cleaved to form the siRNA and longer dsRNA molecules that are cleaved to form siRNA or shRNA.

The terms "to knockdown" or "knocking down," as used herein, refer to the process of partially or completely inhibiting or altering the expression of a nucleic acid through the use of RNA interference. A "knockdown animal," e.g., "knockdown mouse," refers to an animal in which the expression of one or more targeted genes has been inhibited or altered by RNA interference.

The terms "target," targeting" and/or "targeted," as used herein, refer to the binding, annealing or hybridization of a nucleotide sequence (e.g., a siRNA) to a specific, complementary (either completely complementary or of sufficient complementarity to allow for hybridization) nucleotide sequence, i.e., a target nucleotide sequence (e.g., a mRNA).

The term "specifically binds," as used herein, refers to a molecule (e.g., a siRNA) that binds to a target sequence (e.g., a mRNA) with at least about two-fold greater affinity as compared to any non-target sequence, e.g., at least about 5-, 10-, 20-, 50-, or 100-fold greater affinity.

The terms "expression is decreased," "expression is inhibited," "decreased expression," "increased expression" and the like as used herein, refer to a decrease or inhibition in the level of expression of a CYP enzyme gene and/or a decrease or inhibition of activity and/or function of a CYP enzyme in an animal or in a cell of an animal to which has been delivered a siRNA of this invention as compared to an animal or cell in the absence of delivery of the siRNA. The decrease or inhibition may be due, e.g., to a decrease in the amount of mRNA encoding the enzyme, a decrease in translation of the mRNA into the enzyme, and/or a combination these and/or other factors.

The present invention relates to siRNA molecules targeted to RNAs encoding two or more enzymes of a CYP subfamily of cytochrome P450 enzymes. In some embodiments, the CYP subfamily can be Cyp2a, Cyp2b, Cyp2c, Cyp2d, Cyp2j, Cyp3a, Cyp4a, and/or Cyp4f. In one embodiment, the CYP subfamily is Cyp2b. In one embodiment, a single siRNA molecule is targeted to RNAs encoding two or more, three or more, four or more, five or more, or all of the enzymes of a CYP subfamily. In another embodiment, two or more different siRNA molecules, e.g., 2, 3, 4, 5, 6, 7, 8, 9, or 10 different siRNA molecules, are targeted to RNAs encoding two or more, three or more, four or more, five or more, or all of the enzymes of a CYP subfamily. In one embodiment, the CYP subfamily is a rodent CYP subfamily, e.g., a mouse CYP subfamily. In one embodiment, the mouse Cyp1a family comprises the Cyp1a1 and Cyp1a2 genes. In one embodiment, the mouse Cyp1b family comprises the Cyp1b1 gene. In one embodiment, the mouse Cyp2a family comprises the Cyp2a4, Cyp2a5, Cyp2a12, and Cyp2a22 genes or any combination thereof. In one embodiment, the mouse Cyp2b family comprises the Cyp2b9, Cyp2b10, Cyp2b13, Cyp2b19, and Cyp2b23 genes or any combination thereof. In one embodiment, the mouse Cyp2c family comprises the Cyp2c29, Cyp2c37, Cyp2c38, Cyp2c39, Cyp2c40, Cyp2c44, Cyp2c50, Cyp2c54, Cyp2c55, Cyp2c65, Cyp2c66, Cyp2c67, Cyp2c68, Cyp2c69, and Cyp2c70 genes or any combination thereof. In one embodiment, the mouse Cyp2j family comprises the Cyp2j5, Cyp2j6, Cyp2j7, Cyp2j8, Cyp2j9, Cyp2j1, Cyp2j12, and Cyp2j13 genes or any combination thereof. In one embodiment, the mouse Cyp2d family comprises the Cyp2d9, Cyp2d10, Cyp2d11, Cypd12, Cyp2d13, Cyp2d22, Cyp2d26, Cyp2d34, and Cyp2d40 genes or any combination thereof. In one embodiment, the mouse Cyp2e family comprises the Cyp2e1 gene. In one embodiment, the mouse Cyp3a family comprises the Cyp3a11, Cyp3a13, Cyp3a16, Cyp3a25, Cyp3a41, Cyp3a44, Cyp3a57, and Cyp3a59 genes or any combination thereof. In one embodiment, the mouse Cyp4a family comprises the Cyp4a10, Cyp4a12, Cyp4a14, Cyp4a29, Cyp4a30, Cyp4a31, and Cyp4a32 genes or any combination thereof. In one embodiment, the mouse Cyp4f family comprises the Cyp4f13, Cyp4f14, Cyp4f15, Cyp4f16, Cyp4f17, Cyp4f18, Cyp4f37, Cyp4f39, and Cyp4f40 genes or any combination thereof. The nucleotide sequence of each of these genes and any other CYP gene is available in publicly accessible sequence databases, e.g., the GenBank® database, and as such are incorporated by reference herein. Each siRNA is targeted to a sequence in a CYP subfamily gene that is highly conserved among multiple members of the same CYP subfamily. In one embodiment, a single siRNA is targeted to a sequence that is highly conserved among all members of the subfamily. In another embodiment, two or more siRNAs (e.g., 3, 4, 5, 6 or more siRNAs) are targeted to one or more sequences that are highly conserved among members of the subfamily such that multiple members and/or each member of the subfamily is targeted. When multiple siRNAs are used, they may target the same sequence, overlapping sequences, and/or separate sequences on CYP subfamily genes.

In one embodiment of the invention, a siRNA can have a length of about 12 to about 30 nucleotides, e.g., about 18 to about 25 nucleotides, e.g., about 20 to about 22 nucleotides.

In one embodiment of the invention, the siRNA comprises the nucleotide sequence of one or more than one of SEQ ID NOS:1-32 as shown in Table 2. In a further embodiment, the siRNA consists of or consists essentially of the nucleotide sequence of one or more than one of SEQ ID NOS:1-32. In another embodiment, the siRNA comprises a nucleotide sequence that is at least 70% (e.g., at least 75%, 80%, 85%, 90%, 95%, 97%, or 99%) identical to the nucleotide sequence of one or more than one of SEQ ID NOS:1-32. In another embodiment, the siRNA comprises a nucleotide sequence that is at least 70% (e.g., at least 75%, 80%, 85%, 90%, 95%, 97%, or 99%) identical to a fragment of the nucleotide sequence of one or more than one of SEQ ID NOS:1-32 of at least 10 contiguous nucleotides, e.g., at least 11, 12, 13, 14, 15, 16, 17, 18, 19, or 20 contiguous nucleotides. In one embodiment of the invention, the siRNA consists of or consists essentially of a nucleotide sequence that is at least 70% (e.g., at least 75%, 80%, 85%, 90%, 95%, 97%, or 99%) identical to the nucleotide sequence of one or more than one of SEQ ID NOS:1-32. In another embodiment, the siRNA consists of or consists essentially of a nucleotide sequence that is at least 70% (e.g., at least 75%, 80%, 85%, 90%, 95%, 97%, or 99%) identical to a fragment of the nucleotide sequence of one or more than one of SEQ ID NOS:1-32 of at least 10 contiguous nucleotides, e.g., at least 11, 12, 13, 14, 15, 16, 17, 18, 19, or 20 contiguous nucleotides.

TABLE 2

| CYP Subfamily | Sequence |
|---|---|
| Cyp2a | GCCAAGGTCCATGAGGAGATT (SEQ ID NO: 1) |
| Cyp2a | GACAAGGGACAGTTGAAGAAG (SEQ ID NO: 2) |
| Cyp2a | CCCAAAGACTTCAACCCAAAG (SEQ ID NO: 3) |
| Cyp2b | AAGAACACTGAGGTGTACCCC (SEQ ID NO: 4) |
| Cyp2b | AAGGAGATTGATCAGGTGATC (SEQ ID NO: 5) |
| Cyp2b | CAGGAAAGCGCATTTGTCTTG (SEQ ID NO: 6) |
| Cyp2c | GTGCTCCCTGCAATGTCATCT (SEQ ID NO: 7) |
| Cyp2c | GTGCTCCTTGCAATGTCATCT (SEQ ID NO: 8) |
| Cyp2c | GTGCTCCATGCAATGTCATCT (SEQ ID NO: 9) |
| Cyp2c | GTGCTCCCTCCAATGTGATCT (SEQ ID NO: 10) |
| Cyp2c | GTGTTCCCTGCAATGTGATCT (SEQ ID NO: 11) |
| Cyp2c | GTGCTCCCTGCAACGTGATCT (SEQ ID NO: 12) |
| Cyp2d | TCCAGAGATGGCAGACCAGGC (SEQ ID NO: 13) |
| Cyp2d | ATGGAGCTCTTCCTCTTCTTC (SEQ ID NO: 14) |
| Cyp2d | CCTCTTCTTCACCTGCCTCCT (SEQ ID NO: 15) |
| Cyp2d | CCCAGGGCCACTTTGTGAAGC (SEQ ID NO: 16) |
| Cyp2j | GACAGTTTAAGAAGAGAGAAT (SEQ ID NO: 17) |
| Cyp2j | GTTTGTGAAGAAGTATGGAAA (SEQ ID NO: 18) |
| Cyp2j | CAGTTTGATTTAGATGTGTCA (SEQ ID NO: 19) |
| Cyp2j | CATGCCCTACACCAATGCTGT (SEQ ID NO: 20) |
| Cyp3a | CCAACCTGAAAGGTTCAGCAA (SEQ ID NO: 21) |
| Cyp3a | CCTGAAAGGTTCAGCAAGGAG (SEQ ID NO: 22) |
| Cyp3a | GGAACTGCATTGGCATGAGGT (SEQ ID NO: 23) |

TABLE 2-continued

| CYP Subfamily | Sequence |
|---|---|
| Cyp3a | CCTTTGGAAATGGACCCAGGA: (SEQ ID NO: 24) |
| Cyp4a | CCAACAGAGATGCAGAGAGGA (SEQ ID NO: 25) |
| Cyp4a | CATGTGCATCAAGGAGGCCCT (SEQ ID NO: 26) |
| Cyp4a | GCCAAATCCAGAGGTGTTTGA (SEQ ID NO: 27) |
| Cyp4f | AGGAACTGCATAGGACAGACT (SEQ ID NO: 28) |
| Cyp4f | GGCGCTGACTCTGCTGCGCTT (SEQ ID NO: 29) |
| Cyp4f | GGACAGCCTGCAGAAATGTGT (SEQ ID NO: 30) |
| Cyp4f | GGACAGCCTTCAGAAATGTGT (SEQ ID NO: 31) |
| Cyp4f | AAGGATGAAGATGGAAAGGAG (SEQ ID NO: 32) |

In some embodiments, for inhibition of the Cyp2a subfamily in the mouse, one or more siRNAs comprising, consisting essentially of, and/or consisting of a sequence selected from SEQ ID NOS:1-3 may be used. In one embodiment, the siRNA of SEQ ID NO:3 can be used to inhibit all of the genes in the Cyp2a subfamily. In a further embodiment, two separate target sequences can be used, wherein at least two different siRNAs are delivered to a cell of the mouse. In one embodiment, all three siRNAs can be delivered.

In some embodiments, for inhibition of the Cyp2b subfamily in the mouse, one or more siRNAs comprising, consisting essentially of, and/or consisting of a sequence selected from SEQ ID NOS:4-6 may be used. A single target sequence is present in all of the genes in the Cyp2b subfamily, so any one of the siRNAs can be delivered to a cell of the mouse. In other embodiments, two or three of the siRNAs may be delivered, e.g., to enhance the inhibition of expression.

In some embodiments, for inhibition of the Cyp2c subfamily in the mouse, one or more siRNAs comprising, consisting essentially of, and/or consisting of a sequence selected from SEQ ID NOS:7-12 may be used. In some embodiments, multiple siRNAs can be delivered to a cell of the mouse to target all of the genes of the Cyp2c subfamily, e.g., at least 3, 4, 5, or 6 of the siRNAs. In another embodiment, 1 or 2 siRNAs can be delivered to inhibit the expression of specific genes within the Cyp2c subfamily without inhibiting others. For example, the siRNA of SEQ ID NO:7 targets the Cyp2c40, Cyp2c50, Cyp2c67, Cyp2c68, and Cyp2c69 genes, the siRNA of SEQ ID NO:8 targets the Cyp2c37, Cyp2c65, and Cyp2c66 genes, and the siRNA of SEQ ID NO:9 targets the Cyp2c29, Cyp2c38, and Cyp2c39 genes.

In some embodiments, for inhibition of the Cyp2d subfamily in the mouse, one or more siRNAs comprising, consisting essentially of, and/or consisting of a sequence selected from SEQ ID NOS:13-16 may be used. A single target sequence is present in all of the genes in the Cyp2d subfamily, so any one of the siRNAs may be delivered to a cell of the mouse. In other embodiments, two or three of the siRNAs may be delivered, e.g., to enhance the inhibition of expression.

In some embodiments, for inhibition of the Cyp2j subfamily in the mouse, one or more siRNAs comprising, consisting essentially of, and/or consisting of a sequence selected from SEQ ID NOS:17-20 may be used. Two siRNAs selected from SEQ ID NOS:17-19 can be delivered to a cell of the mouse to target all of the genes in the Cyp2j subfamily (e.g., the siRNAs of SEQ ID NOS:17 and 18), while the siRNA of SEQ ID NO:20 targets all of the Cyp2j subfamily genes.

In some embodiments, for inhibition of the Cyp3a subfamily in the mouse, one or more siRNAs comprising, consisting essentially of, and/or consisting of a sequence selected from SEQ ID NOS:21-24 may be used. In one embodiment, all four siRNA sequences can be delivered to target all of the genes in the Cyp3a subfamily.

In some embodiments, for inhibition of the Cyp4a subfamily in the mouse, one or more siRNAs comprising, consisting essentially of, and/or consisting of a sequence selected from SEQ ID NOS:25-27 may be used. In some embodiments, a siRNA of SEQ ID NO:25 and a siRNA of SEQ ID NO:26 can be delivered to a cell of the mouse to target all of the genes in the Cyp4a subfamily. In one embodiment, three siRNA sequences can be delivered.

In some embodiments, for inhibition of the Cyp4f subfamily in the mouse, one or more siRNAs comprising, consisting essentially of, and/or consisting of a sequence selected from SEQ ID NOS:28-32 may be used. In some embodiments, at least three of the sequences (e.g., the siRNAs of SEQ ID NOS:28-30) can be delivered to a cell of the mouse to target all of the genes in the Cyp4f subfamily. In one embodiment, at least four or all five siRNA sequences can be delivered.

In one embodiment, of the invention, CYP gene target sequences can be selected that have limited homology to the corresponding human CYP subfamily gene(s). Targets with limited homology are advantageous for performing studies on human CYP genes in mice in which the corresponding subfamily has been knocked down, as the siRNAs targeted to the mouse CYP genes would not be expected to inhibit the expression of the exogenous corresponding human gene. Limited homology, as used herein, refers to target sequences having less than 90% sequence identity to the corresponding human sequence, e.g., less than 85%, 80%, 75%, or 70% sequence identity. Non-limiting examples of limited homology for a typical siRNA target region of 21 nucleotides include 18 of 21 matching nucleotides or less, e.g., 17 of 21, 16 of 21, 15 of 21, 14 of 21, or less. For example, each of the siRNAs of SEQ ID NOS:5-6 targeted to the Cyp2b subfamily exhibit low homology to the corresponding human Cyp2b6 gene. Similarly, siRNAs of SEQ ID NOS:25-27 (Cyp4a) and siRNAs of SEQ ID NOS:28-32 (Cyp4f) exhibit little homology with the corresponding human genes. For the Cyp2j family, the siRNA of SEQ ID NO:20 is ideal for knocking down all of the genes in the subfamily but is 100% homologous to the corresponding human sequence, so it would not be suitable for use in embodiments wherein an exogenous human Cyp2j gene is to be expressed in a mouse. However, the other siRNA sequences targeted to Cyp2j (SEQ ID NOS: 17-19) show no homology with the corresponding human gene.

One aspect of the invention relates to a vector comprising a polynucleotide encoding the siRNA of the invention. In one embodiment, the vector comprises polynucleotides encoding two or more different siRNAs of the invention. The vector may be any type of vector suitable for expressing a siRNA either in vitro or in a cell, e.g., a viral vector (such as a lentiviral vector) or a plasmid vector and may be suited for use in any type of cell, such as mammalian, insect, plant, fungal, or bacterial cells. For example, viral vectors can be used for carrying siRNA expression cassettes and such vectors deliver siRNA to a greater range of cell types and have a persistent silencing effect. Lentiviral vectors incorporate into the genome and therefore lead to persistent protein silencing (Miyoshi et al., *Proc. Natl. Acad. Sci. USA* 94:10319 (1997)). Lentiviral vectors have been used to construct effective, stable shRNA constructs in cell lines, primary cells and mice. Therefore, lentiviral vectors are useful vectors for silencing genes in vivo and for producing stable, germline transmissible transgenic animals. Furthermore, drug-inducible or tissue specific promoters can be used in embodiments in which knockdowns are lethal and/or tissue specific effects need to be studied. This long-term silencing provides for the study of long-term physiological effects and functional genomics in vitro and in vivo, and is useful in gene therapy protocols.

In one embodiment, the polynucleotide encoding the siRNA encodes a shRNA that is processed after expression into the siRNA. In another embodiment, the polynucleotide encodes a dsRNA molecule that is cleaved after expression into siRNA or into shRNA that is then processed to form siRNA. In one embodiment, the polynucleotide encoding the siRNA is operably linked to one or more regulatory elements useful for expressing the siRNA, e.g., a promoter, enhancer, transcription control elements, etc. The promoter may be a constitutive promoter such as the U6 promoter or an inducible promoter. The promoter may be a tissue specific promoter such that siRNA is expressed only in a specific tissue, such as liver (e.g., albumin, prothrombin, or aldolase promoter), intestine (e.g., intestinal fatty acid binding protein promoter), kidney (e.g., uromodulin promoter), skin (e.g. keratin promoter), muscle (e.g., myoD, myosin, or actin promoter), etc. In another embodiment, siRNAs are expressed in a regulatable manner so that the timing and/or level of shRNA expression can be controlled. Examples of regulatable expression systems include the Cre/Lox irreversible system and inducible systems (e.g., doxycycline-inducible) like those available from Addgene (Wiznerowicz et al., *Nature Meth.* 3:682 (2006)). The vector may further comprise a reporter nucleotide sequence (e.g., green fluorescent protein, β-galactosidase) or a selectable marker (e.g., thymidine kinase) the expression of which can be used to identify cells and animals comprising the vector.

In another embodiment, the invention relates to a cell comprising the siRNAs of the invention. The cell may be any type of cell, e.g., mammalian, insect, plant, fungal, or bacterial cells. The cell can be isolated or the cell can be in a subject (e.g., a mouse or other animal). In one embodiment, the cell is a mouse cell. In a further embodiment, the cell is a hepatocyte. In one embodiment, the cell comprises two or more different siRNAs. In another embodiment, the cell comprises a vector that expresses the siRNA or a precursor of the siRNA.

The siRNAs of the invention may by produced by any method known to those of skill in the art and as described herein. In one embodiment, siRNAs may be produced by chemical synthesis of oligonucleotides and/or ligation of shorter oligonucleotides. Another embodiment of the present invention relates to polynucleotides encoding the siRNAs of the invention. The polynucleotides may be used to express the siRNAs, e.g., by in vitro transcription, polymerase chain reaction amplification, and/or cellular expression. The polynucleotides may be DNA or RNA and may be single-stranded or double-stranded.

In one aspect of the invention, the siRNAs are modified to increase the half-life of the siRNAs in a cell or after delivery to a subject. In one embodiment of the invention, the nucleotides of the siRNAs are linked by phosphate linkages. In another embodiment, one or more of the internucleotide linkages are modified linkages, e.g., linkages that are resistant to nuclease degradation. The phrase "modified internucleotide linkage" includes all modified internucleotide linkages known in the art or that come to be known and that, from reading this disclosure, one skilled in the art will conclude are useful in connection with the present invention. Internucleotide linkages may have associated counterions, and the term is meant to include such counterions and any coordination complexes that can form at the internucleotide linkages. Modifications of internucleotide linkages include, without limitation, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-5' linkage or 2'-5' linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that can be saturated or unsaturated and/or substituted and/or contain heteroatoms, linkages with morpholino structures, amides, polyamides wherein the bases can be attached to the aza nitrogens of the backbone directly or indirectly, and combinations of such modified internucleotide linkages. In another embodiment, the siRNAs comprise 5'- and/or 3'-terminal blocking groups to prevent nuclease degradation (e.g., an inverted deoxythymidine or hexylamine).

In a further embodiment, the siRNAs are linked to conjugates that increase the circulating half-life, e.g., by decreasing nuclease degradation or renal filtration of the siRNA. Conjugates may include, for example, amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of conjugates include steroids, such as cholesterol, phospholipids, di- and tri-acylglycerols, fatty acids, hydrocarbons that may or may not contain unsaturation or substitutions, enzyme substrates, biotin, digoxigenin, and polysaccharides. Still other examples include thioethers such as hexyl-S-tritylthiol, thiocholesterol, acyl chains such as dodecandiol or undecyl groups, phospholipids such as di-hexadecyl-rac-glycerol, triethylammonium 1,2-di-O-hexadecyl-rac-glycero-3-H-phosphonate, polyamines, polyethylene glycol, adamantane acetic acid, palmityl moieties, octadecylamine moieties, hexylaminocarbonyl-oxycholesterol, farnesyl, geranyl and geranylgeranyl moieties, such as polyethylene glycol, cholesterol, lipids, or fatty acids. Conjugates can also be detectable labels. For example, conjugates can be fluorophores. Conjugates can include fluorophores such as TAMRA, BODIPY, cyanine derivatives such as Cy3 or Cy5 Dabsyl, or any other suitable fluorophore known in the art. A conjugate may be attached to any position on the terminal nucleotide that does not substantially interfere with the desired activity of the siRNA that bears it, for example the 3' or 5' position of a ribosyl sugar. A conjugate substantially interferes with the desired activity of an siRNA if it adversely affects functionality such that the ability of the siRNA to bind to its target mRNA is reduced by greater than 80% in an in vitro binding assay.

Another aspect of the invention relates to kits comprising the siRNAs of the invention. The kits may comprise the siRNAs themselves, polynucleotides encoding the siRNAs, vectors comprising the polynucleotides encoding the siRNAs or suitable for inserting a polynucleotide encoding a siRNA, and/or cells comprising the siRNAs, polynucleotides, or vectors. The kits may comprise a single siRNA or two or more different siRNAs in separate containers and/or pooled in one container. The kits may further comprise other components for use with the siRNAs, polynucleotides, vectors, cells, and cell fractions (e.g., microsomes) of the invention. Examples of other components include, without limitation, buffers, solutions, cell culture media, reagents, restriction enzymes, primers, etc. The kits may comprise a carrier, package and/or container that is compartmentalized to receive one or more containers such as vials, tubes, and the like, each of the container(s) comprising one of the separate elements.

Another aspect of the invention relates to methods of decreasing or inhibiting expression of two or more genes from a CYP subfamily in a non-human animal, comprising delivering to a cell of said animal the siRNAs of the invention. The animal may be any non-human animal, e.g., an animal used in research, e.g., a rodent such as a mouse or rat, guinea pig, rabbit, dog, cat, monkey, etc. In one embodiment, the expression of three or more, four or more, five or more, or all of the genes from a CYP subfamily in a non-human animal is inhibited. In another embodiment, the expression of the CYP subfamily genes is inhibited or decreased by at least about 50%, e.g., at least about 60%, 70%, 80%, 90%, or 95%. The level of inhibition of gene expression can be determined by any method known in the art, including, without limitation, detection of CYP subfamily mRNA levels by hybridization assays, Northern blotting, quantitative PCR, in situ hybridization, etc., and/or by detection of CYP subfamily protein levels by immunoassays, Western blots, etc.

In one embodiment of the invention, the methods involve delivering to the animal or a cell of the animal a siRNA targeted to a nucleotide sequence present in two or more genes or coding sequences of a Cyp subfamily. In another embodiment, two or more different siRNAs targeted to the same nucleotide sequence or to different nucleotide sequences present in one or more genes within the CYP subfamily are delivered to the animal. The siRNAs may be delivered to the non-human animal by any protocol well known in the art and as described herein. The siRNAs may be delivered directly to the animal, e.g., by injection into the circulation or into a tissue or body cavity of the animal. The siRNAs may be delivered to the animal in the form of a vector comprising a polynucleotide encoding the siRNA or a precursor of the siRNA. The vector may encode a single siRNA in one or more than one copy and/or multiple different siRNAs in one or more than one copy of each different siRNA. In a different embodiment, two or more vectors each encoding different siRNAs are delivered to the animal. The vector may be delivered directly to the animal, e.g., by injection into the circulation or into a tissue or body cavity of the animal. In some embodiments, the vector may be introduced into a cell and the cell can then be delivered to the animal. In one embodiment, the vector is introduced into a cell of an early stage embryo, e.g., by microinjection into the perivitelline space of an embryo, e.g., a 0.5 day embryo. In another embodiment, the vector is co-incubated with zygotes. In a further embodiment, the vector can be introduced by pronuclear injections. The injected embryos are then implanted into pseudo-pregnant recipients. New-born mice can be screened for the presence of the vector, e.g., by PCR amplification of vector sequences, by detecting expression of a reporter gene nucleotide sequence on the vector such as green fluorescent protein or β-galactosidase, and/or by detecting the presence of siRNAs or a precursor of the siRNAs.

Another aspect of the invention relates to a non-human animals in which expression of two or more genes from a CYP subfamily has been decreased or inhibited by delivery of the siRNAs of the invention to a cell of the animal. The animal may be any non-human animal, e.g., an animal used in research, e.g., a rodent such as a mouse or rat, guinea pig, rabbit, dog, cat, non-human primate, etc. In one embodiment, the expression of three or more, four or more, five or more, or all of the genes from a CYP subfamily in a non-human animal has been decreased or inhibited. In another embodiment, the expression of the two or more genes from a CYP subfamily has been decreased or inhibited by at least about 50%, e.g., at least about 60%, 70%, 80%, 90%, or 95%. The level of inhibition of gene expression can be determined by any methods known in the art and as described herein, including, without limitation, detection of CYP subfamily mRNA levels by hybridization assays, Northern blotting, quantitative PCR, in situ hybridization, etc. and/or by detection of CYP subfamily protein levels by immunoassays, Western blots, etc.

In another aspect of the invention, the non-human animal in which expression of two or more genes from a CYP subfamily has been decreased further comprises at least one exogenous polynucleotide encoding a human CYP subfamily enzyme. In one embodiment, the animal comprises a nucleotide sequence encoding human CYP1A1 and/or CYP1A2. In one embodiment, the animal comprises a nucleotide sequence encoding human CYP1B1. In one embodiment, the animal comprises a nucleotide sequence encoding one or more of human CYP2A6, CYP2A7, and/or CYP2A13. In one embodiment, the animal comprises a nucleotide sequence encoding human CYP2B6. In one embodiment, the animal comprises a nucleotide sequence encoding one or more of human CYP2C8, CYP2C9, CYP2C18, and/or CYP2C19. In one embodiment, the animal comprises a nucleotide sequence encoding human CYP1D6. In one embodiment, the animal comprises a nucleotide sequence encoding human CYP2E1. In one embodiment, the animal comprises a nucleotide sequence encoding one or more of human CYP3A4, CYP3A5, CYP3A7, and/or CYP3A43. In one embodiment, the animal comprises a nucleotide sequence encoding human CYP2J2. In one embodiment, the animal comprises a nucleotide sequence encoding one or more of human CYP4 µl and/or CYP4A22. In one embodiment, the animal comprises a nucleotide sequence encoding one or more of human CYP4F2, CYP4F3, CYP4F8, CYP4F11, CYP4F12, and/or CYP4F22.

In another embodiment, the expression of all of the endogenous genes from a CYP subfamily in the animal has been decreased or inhibited so that the function and/or activity of the exogenous human CYP subfamily enzyme can be detected and/or analyzed without interference from the endogenous genes from the CYP subfamily. The exogenous polynucleotide encoding a human CYP subfamily enzyme may be delivered to an animal by any method known in the art, e.g., as the polynucleotide itself, in the form of a vector, in the form of an artificial chromosome, etc. The polynucleotide may be delivered to cells throughout the animal or only to one or more specific tissues within the animal, e.g., to correlate with a specific tissue in which the endogenous genes from a CYP subfamily have been inhibited or decreased. The exogenous polynucleotide may encode a wild-type sequence of the human CYP subfamily enzyme, a specific polymorphism of the human CYP subfamily enzyme and/or a human CYP subfamily enzyme comprising a deletion, insertion, and/or mutation.

One aspect of the invention relates to methods for studying the function of an enzyme of a CYP subfamily of cytochrome P450 enzymes in a non-human animal, comprising decreasing or inhibiting the expression of two or more endogenous genes from a CYP subfamily in the animal by delivering a siRNA of the invention to a cell of the animal, and comparing the phenotype of the animal to the phenotype of a control animal. In one embodiment, the control animal is an animal in which the expression of endogenous CYP subfamily genes has not been decreased or inhibited. The phenotype of the CYP subfamily knockdown animal may be studied by comparing any aspect of the animal, including without limitation histology, physiology, anatomy, morbidity and mortality, metabolism, gene expression, protein production, enzyme activity, etc. Examples of phenotypic traits that may be studied include monitoring the metabolism of a compound administered to the animal, histological analysis of the liver, and measurement of serum chemistry and/or other clinical analytes.

One aspect of the invention relates to methods for determining the role of an enzyme of a CYP subfamily of cytochrome P450 enzymes in the metabolism, elimination, and/or homeostasis of a compound in a non-human animal, comprising delivering said compound to an animal in which the expression of two or more endogenous genes from a CYP subfamily has been decreased or inhibited by delivery of a siRNA of the invention to a cell of the animal, and comparing the metabolism, elimination, and/or homeostasis of said compound after delivery to a control animal. In one embodiment, the control animal is an animal in which the expression of CYP subfamily genes has not been decreased. In one embodiment, the compound may be an endobiotic, e.g., an endogenous compound known to be acted on by cytochrome P450 enzymes, including without limitation steroids, cholesterol, fatty acids, eicosanoids, and/or bile acids. In another embodiment, the compound can be a xenobiotic, including without limitation a pharmaceutical compound, an industrial chemical, an environmental chemical, and/or a pesticide. The methods may be used to study the activation and/or detoxification of a compound. Following administration of the compound to the animal, the fate of the compound and/or its metabolites may be analyzed by detecting an amount and/or activity of the compound and/or its metabolites in tissues, blood, plasma, serum, urine, feces, saliva, mucosal secretions, etc. The compound to be delivered to the animal may be labeled (e.g., radioactive, fluorescent, chromogenic) for easier detection of the compound and/or its metabolites.

A further aspect of the invention relates to methods for studying the function of an exogenous human enzyme of a CYP subfamily of cytochrome P450 enzymes in a non-human animal, comprising expressing a human CYP subfamily gene in an animal in which the expression of two or more endogenous genes from a CYP subfamily has been decreased or inhibited by delivery of a siRNA of the invention to a cell of the animal, and comparing the phenotype of the animal to the phenotype of a control animal.

In one embodiment, a polynucleotide encoding the exogenous human CYP subfamily enzyme is delivered to at least one cell of the animal. The polynucleotide may be delivered itself and/or in the form of a vector and/or artificial chromosome. The human CYP subfamily polynucleotide may be expressed in all cells of the animal or in specific cells or tissues, e.g., correlating with specific cells or tissues in which expression of the endogenous CYP subfamily genes have been decreased or inhibited. The polynucleotide encoding the human CYP subfamily enzyme may be part of the vector encoding a siRNA of the invention or part of a separate vector, and may be delivered to the non-human animal at the same time as the vector encoding the siRNA, e.g., by perivitelline injection of an embryo. In another embodiment, the exogenous polynucleotide encoding the human CYP subfamily enzyme may be delivered to the animal at a different time and/or location as the siRNA. The human CYP gene may be a polymorphic variant or a gene encoding a mutant form of a human CYP subfamily enzyme such as a deletion, addition, and/or substitution mutant. These variants can be expressed in the CYP subfamily knockdown animal in order to study the function of the human CYP enzyme and determine the effects of variations in the sequence on enzyme function. In one embodiment, the control animal is an animal in which no exogenous human CYP enzyme is present. In another embodiment, the control is an animal in which an exogenous wild-type human CYP enzyme is produced from an exogenous nucleotide sequence.

One aspect of the invention relates to methods for identifying a siRNA capable of decreasing the expression of two or more genes in a multi-gene family. In one embodiment, the methods comprise comparing the nucleotide sequence of two or more genes in the multi-gene family to each other, identifying a segment of at least about 12 contiguous nucleotides (e.g., at least about 13, 14, 15, 16, 17, 18, 19, or 20 nucleotides) that is at least about 70% identical (e.g., at least about 75%, 80%, 85%, 90%, 95%, 97%, or 99% identical) in each of the two or more genes, and preparing a siRNA specific for the identified segment according to methods well known in the art and as described herein. The sequence comparison may be carried out manually or may be performed using sequence comparison software as is well known in the art. The methods may further comprise the step of testing the siRNA for its ability to decrease or inhibit expression of the two or more genes of the multi-gene family. In one embodiment, the multi-gene family is a CYP subfamily.

The present invention is explained in greater detail in the following non-limiting Examples.

EXAMPLE 1

Identification of Cyp2b Gene Target Regions and Preparation of siRNAs

The Cyp2b gene subfamily was chosen because initial studies indicated that it is possible to knockdown all of the Cyp2b subfamily members from mice with only one siRNA construct and still humanize the mice with CYP2B6 and because the role of the Cyp2b subfamily in hormone homeostasis, bile acid metabolism, organophosphate toxicity, etc., could be examined. There are five regions among the five mouse Cyp2b gene subfamily members that show high homology. Three of these targets were chosen for preparation of shRNA constructs. The three targets (shaded areas KD1, KD2, and KD3) are shown in FIG. 1 that would allow for the knockdown all of the Cyp2b gene subfamily members. Constructs directed to the three targets are tested in vitro both separately and together to test their efficiency. In vivo, one or more siRNAs are used to ensure that the knockdown works and to increase the potency of the knockdown. However, each construct is tried separately because construct #2 (KD2) that targets the Cyp2b subfamily at about nucleotide 1170 to 1195 is poorly conserved between humans and mice and is an ideal target for silencing mouse Cyp2b when a humanized mouse is made. 18/21 bp are the same when comparing mouse to human in construct #1 and construct #3; 14/21 bp are the same between mouse and human for construct #2, making it highly unlikely that a siRNA targeted to KD2 would effect expression of a human CYP2B6 transgene (FIG. 1). Both construct #1 and #3 also have potential for use in humanized mice because only 18/21 bp are the same. Lastly, the shRNA constructs described herein do not show significant homology to other P450 genes.

The siRNAs directed to KD1, KD2, and KD3 were designed using rules described by MIT (www.broad.mit.edu/genome_bio/trc/rules.html) and/or tools available on the Ambion website (Ambion-Applied Biosystems, Austin, Tex.). The siRNA constructs were chemically synthesized by Sigma-Genosys and HPLC purified. The sense strand of the two siRNAs that target KD1 and KD2, respectively, including BamH1 and HindIII cloning sites, are 5'-GATCCGGAGAT-TGATCAGGTGATC-ttcaagagaGATCACCTGAT-CAATCTCCTT-TTTTGGAAA-3' (SEQ ID NO:51) and 5'-GATCCGAACACTGAGGTGTACCCC-ttcaa-gagaGGGGTACACCTCAGTGTTCTT-TTTTGGAAA-3' (SEQ ID NO:52), respectively. The siRNA construct for KD3 was synthesized by Genscript 5'-GGATCCCGCAAGA-CAAATGCGCTTTCCTGttgatatccg-cAGGAAAGCGCATTTGT CTTGTTTTTTCCAACTC-GAG-3' (SEQ ID NO: 53). The loop sequences are shown in lowercase and the reverse siRNA sequence is in italics. The shRNA KD1 and KD2 templates were diluted to 1 µg/µl and annealed prior to ligation into the vector pSilencer 5.1™ with T4 DNA ligase as described by the manufacturer (Ambion). The Genscript pRNAT-U6.2/Lenti system was used for the production of KD2 and KD3. This system is tagged with GFP as a convenient marker of transduction or transfection. Both RT-PCR and DNA sequencing confirmed the presence of the targeting constructs in the pSilencer™ plasmid.

As a control, pRNAT-U6.2/Lenti scrambled shRNA that contains a scrambled shRNA sequence instead of the Cyp2b specific shRNAs is used. shRNA expressing lentiviruses are generated as previously described (Llano et al., *Science* 314: 461 (2006)) using a commercially available kit from Invitrogen (ViraPower™ Lentiviral Support Kit). Briefly, 293T cells are transfected with a tri-plasmid system consisting of the pRNAT-U6.2/Lenti or pSilencer 5.1-U6 Cyp2b shRNA, pΔR8.9 and pVSV-G and forty-eight hours after transfection viral supernatant is collected, filtered through 0.45 µm low protein binding filters, and concentrated by ultracentrifugation on a 10% sucrose cushion. Viral stocks are stored at −80° C. until use.

Several constructs were prepared in the pRNAT-U6.2/Lenti plasmid (Genscript, Piscataway, N.J.), including constructs that will knockdown Cyp2a, Cyp2b, Cyp2d, and Cyp4a function. Table 3 provides the construct for each of the siRNAs built. The underlined areas of the constructs are the sense and anti-sense strands that recognize and target CYP mRNA for destruction. Each of these constructs recognizes multiple isoforms of a mouse subfamily without recognizing the corresponding human subfamily members. Scrambled DNA is a control set of siRNA that does not recognize any murine mRNAs as determined by BLAST searching. This shRNA construct will be used to make control mice. Cyp2b-KD1 was made and inserted into a different retroviral based plasmid (pSilencer 5.1-U6).

TABLE 3

| CYP FAMILY | CONSTRUCT |
|---|---|
| Scrambled | GGATCCCGACGATTCGAGGCGCAGTGATTTGATATCCG ATCACTGCTCCTCGAATCGTCTTTTTTCCAACTCGAG (SEQ ID NO: 54) |
| Cyp2a-KD1 | GGATCCCGCTTTGGGTTGAAGTCTTTGGGTTGATATCCG CCCAAAGACTTCAACCCAAAGTTTTTTCCAACTCGAG (SEQ ID NO: 55) |
| Cyp2b-KD1 | GGATCCCAAGGAGATTGATCAGGTGATCTTGATATCCG GATCACCTGATCAATCTCCTTTTTTTTCCAACTCGAG (SEQ ID NO: 56) |
| Cyp2b-KD2 | GGATCCCAAGAACACTGAGGTGTACCCCTTGATATCCG GGGGTACACCTCAGTGTTCTTTTTTTTCCAACTCGAG (SEQ ID NO: 57) |
| Cyp2b-KD3 | GGATCCCGCAAGACAAATGCGCTTTCCTGTTGATATCCG CAGGAAAGCGCATTTGTCTTGTTTTTTCCAACTCGAG (SEQ ID NO: 58) |
| Cyp2d-KD1 | GGATCCCGCCTGGTCTGCCATCTCTGGATTGATATCCGT CCGTTCCAGAGATGGCAGACCAGGCTTTTTTCCAACTCGAG (SEQ ID NO: 59) |
| Cyp2d-KD2 | GGATCCCGCCTCTTCTTCACCTGCCTCCTTTGATATCCG AGGAGGCAGGTGAAGAAGAGGTTTTTTCCAACTCGAG (SEQ ID NO: 60) |
| Cyp4a-KD1 | GGATCCCAGGGCCTCCTTGATGCACATGTTGATATCCG CATGTGCATCAAGGAGGCCCTTTTTTTCCAACTCGAG (SEQ ID NO: 61) |
| Cyp4a-KD2 | GGATCCCGCCAACAGAGATGCAGAGAGGATTGATATCCG TCCTCTCTGCATCTCTGTTGGTTTTTTCCAACTCGAG (SEQ ID NO: 62) |

EXAMPLE 2

Analysis of siRNA Function

The efficacy of the shRNA constructs is tested in mouse primary hepatocytes and in the knockdown mice by quantitative real-time PCR (Q-PCR) to detect destruction of mRNA and Western blotting to detect suppression of protein synthesis.

In order to carry out the protein measurements, a high affinity specific antibody was produced. The GenScript Corporation (Piscataway, N.J.) antigen design tool was used to design a basic peptide with high antigenicity. A cysteine was added to the C-terminus of the designed peptide (LHDPQY-FEQPDSFN-C (SEQ ID NO:63)), and conjugated to Keyhole Limpet Hemocyanin (KLH). This peptide is poorly conserved between Cyp2b and Cyp2a (and other P450s), and therefore should be specific for only Cyp2b. Two rabbits were injected 4× each and approximately 160 ml of blood was collected and pooled from the rabbits. The antibody was purified by affinity purification through an affinity column containing conjugated peptide.

FIG. 2 shows that newly produced Cyp2b antibody (FIG. 2A) exhibits greater specificity and sensitivity than Gentest's Cyp2b antibody (FIG. 2B), and much greater affinity than the Cyp2b10 antibody from Dr. Randy Rose (FIG. 2C). Only 25 µg of protein were needed to observe Cyp2b from untreated mouse liver microsomes using the new antibody, as compared to the approximately 100 µg of protein needed to observe Cyp2b by Western blotting using the other two antibodies. Furthermore, only Cyp2a (lower band) is observed via Western blotting of the untreated microsomes using the Gentest antibody. This antibody only shows Cyp2b in TCPOBOP-induced microsomes. Overall, the new antibody is a great improvement over other antibodies as it shows greater specificity and much greater sensitivity for Cyp2b.

To evaluate the knockdown efficiency of the different Cyp2b shRNAs, untreated and TCPOBOP treated mouse primary hepatocytes are transduced at different multiplicity of infection (10, 30, 90 and 270) with lentivirus expressing the two Cyp2b specific shRNAs and the control shRNA, respectively. Cyp2b protein levels are analyzed one week after transduction by immunoblotting with the newly developed rabbit anti-Cyp2b polyclonal antibody. Briefly, transduced cells are harvested by scraping and microsomes prepared by differential centrifugation (Van der Hoeven et al., *J. Biol. Chem.* 249:6302 (1974)) in the presence of aprotinin, leupeptin, and PMSF as protease inhibitors. Protein concentrations are quantified using commercially available reagents (Bio-Rad, Hercules, Calif.). 25 µg of microsomal protein is separated electrophoretically on a 10% polyacrylamide gel (SDS-PAGE), transferred to nitrocellulose and incubated with the Cyp2b antibody and a goat anti-rabbit secondary antibody, followed by detection with a chemiluminescent kit according to the manufacturer's directions (Bio-Rad). Chemoluminescence is quantified on a Chemi-Doc system with Quantity One® software. The lentivirus achieving the most effective Cyp2b knockdown is selected for future experiments.

Q-PCR is performed to determine the efficacy of shRNA knockdown of the Cyp2b gene subfamily. Total RNA is isolated using a modified guanidinium thiocyanate-phenol-chloroform extraction protocol with TRI-reagent (Sigma, St. Louis, Mo.) according to the manufacturer's specifications followed by DNAse (Promega Corporation, Madison Wis.) treatment to remove residual genomic DNA. RNA is quantified spectrophotometrically and stored at −80° C. Reverse transcription is performed to create cDNA using MMLV-RT, a dNTP mixture, and random decamers. cDNA is stored at −20° C. Q-PCR is performed as described previously (Roling et al., *Mar. Environ. Res.* 57:377 (2004)). Briefly, to generate a standard curve and determine PCR efficiency, cDNA is combined and a 2×, 1:1, 1:10, 1:100, and 1:1000 dilution made. Most samples are diluted 1:10, but some high expression genes or genes that are highly induced are diluted 1:40 (18S). Amplifications are performed in triplicate using a 96-well MyiQ™ Real-Time PCR Detection System (Bio-Rad) with 0.25× SybrGreen as the fluorescent double strand-intercalating agent to quantify gene expression. Specific Q-PCR primers are provided in Table 4. The advantage of Q-PCR is having enough material to investigate a decrease of several Cyp2b isoforms as well as confirm that other P450 subfamilies are unaffected (Cyp3a, 2c).

TABLE 4

Validated mouse quantitative real-time PCR (Q-PCR) primers

| Gene | Primer Sequence | |
|---|---|---|
| Cyyp2a4 | Forward AGCAGGCTACCTTCGACTGG | (SEQ ID NO: 64) |
| | Reverse GCTGCTGAAGGCTATGCCAT | (SEQ ID NO: 65) |

TABLE 4-continued

Validated mouse quantitative real-time PCR (Q-PCR) primers

| Gene | Primer Sequence | |
|---|---|---|
| Cyp2b9 | Forward CTGAGACCACAAGCGCCAC | (SEQ ID NO: 66) |
| | Reverse CTTGACCATGAGCAGGACTCC | (SEQ ID NO: 67) |
| Cyp2b10 | Forward CTGAATCCGCTCCTCCACACTC | (SEQ ID NO: 68) |
| | Reverse TGAGCCAACCTTCAAGGAATAT | (SEQ ID NO: 69) |
| Cyp2b13 | Forward GAACTGAGACTACCAGCACCACTCCT | (SEQ ID NO: 70) |
| | Reverse TGAGCATGAGCAGGAAACCACT | (SEQ ID NO: 71) |
| Cyp2c29 | Forward GGCCTCAAAGCCCTACTGTCA | (SEQ ID NO: 72) |
| | Reverse AACGCCAAAACCTTTAATC | (SEQ ID NO: 73) |
| Cyp2c37 | Forward ATACTCTATATTTGGGCAGG | (SEQ ID NO: 74) |
| | Reverse GTTCCTCCACAAGGCAAC | (SEQ ID NO: 75) |
| Cyp2c40 | Forward CATTGAACACTGGCAACATTG | (SEQ ID NO: 76) |
| | Reverse GTCACAGGTTACTTCATGCAC | (SEQ ID NO: 77) |
| Cyp3a11 | Forward CTTTCCTTCACCCTGCATTCC | (SEQ ID NO: 78) |
| | Reverse CTCATCCTGCAGTTTTTCTGGAT | (SEQ ID NO: 79) |
| Cyp3a25 | Forward CACATCATTTGGCGTGAACG | (SEQ ID NO: 80) |
| | Reverse TTTCTGCACAAAGGGATCCTG | (SEQ ID NO: 81) |
| Cyp3a41 | Forward GTGGAGAAAGCCAAAGGGATT | (SEQ ID NO: 82) |
| | Reverse GAAGACCAAAGGATCAAAAAAGTCA | (SEQ ID NO: 83) |
| Cyp3a44 | Forward TTGTGGAGGAAGCCAAAAAGTTT | (SEQ ID NO: 84) |
| | Reverse TTGTGGAGGAAGCCAAAAAGTTT | (SEQ ID NO: 85) |
| 18S rRNA | Forward ATGGCCGTTCTTAGTTGGTG | (SEQ ID NO: 86) |
| | Reverse ATGCCAGAGTCTCGTTCGTT | (SEQ ID NO: 87) |
| β-actin | Forward GCTATGTTGCTCTAGACTTCG | (SEQ ID NO: 88) |
| | Reverse CCTCATGGTGCTAGGAGC | (SEQ ID NO: 89) |

Q-PCR results are normalized to the expression of the two housekeeping genes, β-Actin and 18S rRNA. A minimum of forty cycles is run on all real time samples to ensure a log based growth curve. Quantification is done by taking the efficiency curve of the Q-PCR reaction to the power of the threshold cycle ($C_t$). Samples are normalized to reference genes (β-actin and 18S rRNA) quantified for each sample. The formula for calculating normalized gene expression is $$NE = \{E_{ref}\}^{Ct\text{-}ref} / \{E_{target}\}^{Ct\text{-}target}$$

where NE is normalized gene expression, E is the efficiency of amplification for a particular gene, $C_t$ is the threshold cycle, ref is the housekeeping gene (β-actin and 18S rRNA), and target is the gene of interest (Muller et al., *Biotechniques* 32:1372 (2002)).

The efficacy of the Cyp2b-KD2 and Cyp2b-KD3 lentiviral constructs to repress the expression of the Cyp2b subfamily members, Cyp2b9 and Cyp2b10 was tested using primary mouse hepatocytes. Primary mouse hepatocytes were plated in 6-well plates, treated with the CAR activator TCPOBOP to induce Cyp2b subfamily members (especially Cyp2b10) and then infected with either scrambled, Cyp2b-KD2 or Cyp2b-KD3 at a multiplicity of infection (MOI) of 20 and/or 5. The percentage of cells infected based on the presence of green fluorescence using fluorescent microscopy was approximately 65-80+% in KD2 transduced cells at a MOI of 5 and a about 55-70% in KD3 transduced cells at a MOI of 5.

The results demonstrate that the lentiviral constructs reduce the expression of Cyp2b9 and Cyp2b10 mRNA (FIGS. 3A-3D). Cyp2b-KD2 reduced Cyp2b9 and Cyp2b10 expression 75-98%. This is much better than expected given that only 65-80% of the cells were infected. This suggests that the cells that were infected showed a complete abolishment of these Cyp2b subfamily members. Cyp2b-KD3 was not as efficacious. It reduced Cyp2b10 expression 50% following infection of 55-70% of the cells. This is a very good result; however, Cyp2b9 expression was not reduced relative to cells treated with the scrambled shRNA. Lastly, scrambled-shRNA did not reduce Cyp2b9 or Cyp2b10 expression relative to uninfected cells, indicating that it functions well as a control shRNA.

EXAMPLE 3

Production of Cyp2b Knockdown Mouse

Engineered lentiviral particles are microinjected directly into the perivitelline space of mouse embryos or coincubated with denuded embryos (those lacking a zona pellucida after incubation in 0.5× pronase or Tyrode's acidic solution) 0.5 days after fertilization (Rubinson et al., *Nature Genet.* 33:401 (2003); Tiscornia et al., *Proc. Natl. Acad. Sci. USA* 100:1844 (2003); Lois et al., *Science* 295:868-872 (2002). In some embodiments, the lentiviral particles can be designed so that the viral glycoprotein coat adheres to the embryo, has a self-inactivating viral vector containing a Cyp2b shRNA construct and reverse transcriptase to catalyze incorporation into the genome. Embryos are then incubated at 37° C. for at least about one hour up to overnight and 2-cell embryos are implanted into the oviduct of pseudopregnant B6 female mice the following day. Pups are genotyped to test for the presence of the transgene.

Three days prior to lentiviral injections, 5 IU of pregnant mare serum gonadotropin is injected ip into female donor mice. After 47 hours, 5 IU of human chorionic gonadotropin is administered by ip injection and the females are paired with stud males. Females with plugs are sacrificed by cervical dislocation, oviducts collected and placed in flushing and holding medium (FHM) containing hyaluronidase. Embryos are flushed from the oviducts with approximately 1 ml of FHM per horn into a 60 mm dish containing FHM/hyaluronidase medium with KSOM. The embryos are rinsed to remove debris and microinjected with 1 million particles per microliter suspended in PBS. Virus is injected into the perivitelline space with adequate volume to see obvious swelling of the perivitelline space. After 30 eggs are injected, they are placed in a 35 mm dish with three drops of warmed KSOM. Embryos are incubated for at least about one hour up to overnight. The transfection rate should be higher than 90%.

Oviduct implant surgeries are performed the next day by transferring two-cell embryos bilaterally into the oviducts of 0.5 day pseudo-pregnant recipients.

Mice expressing the pRNAT-U.6/Lent controlled shRNA can be screened using the GFP. New born mice are examined with a fluorescence stereomicroscope with GFP-specific filters or with a hand held UV lamp. Screening is performed before the appearance of coat color to avoid reduction of detection sensitivity. Alternatively, mice can be screened using pRNAT specific screening primers (forward 5'-GGATCCCAAGAACACTGAGG-3' (SEQ ID NO:90); reverse 5'-TTATGTAACGCGGAACTCCA-3' (SEQ ID NO:91)) or pSilencer specific screening primers (forward 5'-TTGTACACCCTAAGCCTCCG-3' (SEQ ID NO:92); reverse 5'-GGGTTTATATATCTTGTGGAA-3' (SEQ ID NO:93)) when these systems are used. Mice that show the greatest expression are used as founders for a line and for subsequent study to determine whether Cyp2b is substantially suppressed. In addition, primers specific to the Cyp2b-KD2 (forward 5'-GAGGGCCTATTTCCCATGAT-3' (SEQ ID NO:94); reverse 5'-TCAAGGGGTACACCTCAGTG-3' (SEQ ID NO:95)) or scrambled lentiviral constructs (forward 5'-GAGGGCCTATTTCCCATGAT-3' (SEQ ID NO:96); reverse 5'-AAATCACTGCGCCTCGAAT-3' (SEQ ID NO:97)) have been made for genotyping purposes. These primers should also be useful for quantitative real-time PCR using Sybr-green as the quantitative dye.

Viral particles containing the Cyp2b-KD2 siRNA construct ($2\times10^7$ particles) were coincubated with denuded early stage embryos for two hours at 37° C. The embryos were implanted and mice produced. Tail clippings from the pups were genotyped and one mouse was positive for the Cyp2b-KD2 siRNA construct in its genome.

To measure suppression of Cyp2b, control and knockdown mice are left untreated or injected with TCPOBOP (3 mg/kg ip) (n=3-4). Mice are euthanized, and then livers excised. A portion of the liver is placed in formalin for histology investigations. The rest of the liver is snap frozen in liquid nitrogen, diced, separated into two tubes, and placed in a freezer at −80° C. for further preparation. RNA extraction with TriZol or microsome preparation is performed so that Q-PCR of individual Cyp2b isoforms or Western blots can be performed to quantify the suppression of Cyp2b in the knockdown mice.

EXAMPLE 4

Analysis of Phenotype of Cyp2b Knockdown Mouse

A. Determine the Effects of Cyp2B on Endobiotic (Steroid Hormone, Bile Acid) Metabolism, Elimination, and Homeostasis.

To analyze the phenotype of Cyp2b-knockdown mice, the effects of Cyp2b loss on bile acid homeostasis, toxicity, and steroid hormone levels can be investigated.

Serum chemistry: Eight male and female untreated wild-type and eight male and female untreated Cyp2b-knockdown mice (8-10 weeks old) are anesthetized with isoflurane for blood collection by heart puncture, and euthanized with $CO_2$. Serum is collected, prepared and used to determine total serum bile acid and cholesterol colorimetrically using kits (Diazyme, Poway, Calif.). Alternatively, bile is collected from cannulated mice and biliary cholesterol and bile acid concentrations measured (Diazyme, Poway, Calif.). Serum aldosterone, estradiol, and testosterone concentrations are determined using EIA kits available from Diagnostic Systems Laboratories (Webster, Tex.). Vaginal swabs are collected at the time of blood collection and prior to euthanasia using Richard-Allan Signature Series™ stains (Kalamazoo, Mich.). The maturation index is used to determine the female mice in estrus by identifying increased cornified epithelium in the vagina and determining the percentage of superficial, intermediate, and parabasal cells (Laws et al., *Toxicol. Sci.* 54:154 (2000); Champlin et al., *Biol. Reprod.* 8:491 (1973)).

Histopathology: The mice are placed whole in 10% formalin (Fisher Scientific, Fair Lawn, N.J.) for histological examination of individual tissue sections. Representative sections of the formalin-fixed liver, brain, lung, adrenals, skin, kidneys, intestine, etc. are processed by routine methods, embedded in paraffin, sectioned at 4 μm, stained with hematoxylin and eosin, and coverslipped for histological examination by light microscopy for the presence of pathological lesions or histopathological changes caused by the suppression of Cyp2b gene expression. All samples are coded so that the veterinary pathologist is unaware of the sample's genetic background.

Lithocholic acid (LCA) treatment: CAR-null mice show increased sensitivity to lithocholic acid (LCA), and CAR or PXR activation confers resistance to LCA-induced hepatotoxicity (Xie et al., *Proc. Natl. Acad. Sci. USA* 98:3375 (2001); Saini et al., *Mol. Pharmacol.* 65:292 (2004)). Cyp2b is involved in the metabolism of bile acids. Wild-type and Cyp2b-knockdown mice are fed 8 mg/kg LCA for 4 days (n=5). After 4 days, mice are euthanized, livers excised, and a portion of the liver placed in formalin for Hma staining and histopathological examination as described herein for acetaminophen treatments.

Livers from all of the treated mice are excised, diced and frozen at −80° C. for RNA isolation and protein preparation for future analysis of Cyp2b and other P450 enzyme expression.

B. Test Whether Cyp2B Knockdowns are Sensitive to the Effects of Specific Drugs and Environmental Chemicals.

CAR-null mice show increased sensitivity to zoxazolamine and parathion. There are varying reasons for the differential toxicities, but perturbed P450 expression almost certainly plays a role. Furthermore, Cyp2b is important in the metabolism of both chemicals (Hernandez et al., *Toxicol. Appl. Pharmacol.* 216:186 (2006); Foxenberg et al., *Drug Metab. Dispos.* 35:189 (2007)). Therefore, wild-type and Cyp2b-knockdown mice can be treated with parathion or zoxazolamine. In addition, mice can be treated with parathion or zoxazolamine after pre-treatment with TCPOBOP (n=5/treatment). The purpose of treating mice with the potent CAR activator and Cyp2b-inducer TCPOBOP is to compare mice with very high levels of Cyp2b to those with low levels (TCPOBOP-treated Cyp2b-knockdown) in order to help distinguish the role of Cyp2b in toxicity. Table 5 describes a typical treatment regimen.

TABLE 5

Brief description of treatments to be performed with Cyp2b-knockdown mice

| | |
|---|---|
| Group 1 | Wild-type mice untreated (injected with saline or corn oil). |
| Group 2 | Cyp2b-knockdown mice untreated (injected with saline or corn oil). |
| Group 3 | Wild-type mice treated with a chemical (typically ip). |

TABLE 5-continued

Brief description of treatments to be performed with Cyp2b-knockdown mice

| | |
|---|---|
| Group 4 | Cyp2b-knockdown mice treated with a chemical (typically ip). |
| Group 5 | Wild-type mice treated with TCPOBOP (3 mg/kg) 24 h prior to sham injection. |
| Group 6 | Cyp2b-knockdown mice treated with TCPOBOP (3 mg/kg) 24 h prior to sham injection. |
| Group 7 | Wild-type mice treated with TCPOBOP (3 mg/kg) 24 hours prior to treatment with chemical. |
| Group 8 | Cyp2b-knockdown mice treated with TCPOBOP (3 mg/kg) 24 hours prior to treatment with chemical. |

Zoxazolamine: Wild-type and Cyp2b knockdown mice are injected ip with 300 mg/kg of zoxazolamine in sterile corn oil. In addition, wild-type and Cyp2b-knockdown mice are injected with TCPOBOP (3 mg/kg ip in sterile corn oil) 24 hours prior to treatment (ip injection) with 300 mg/kg of zoxazolamine in sterile corn oil. After injection, initial paralysis is noted, and paralysis time is measured by placing the mice on their backs and measuring the time until they are able to consistently right themselves. Because females are less sensitive than males to zoxazolamine paralysis and wild-type females in general right themselves much sooner, Cyp2b-knockdown female mice should provide stronger data, and therefore female mice can be used for the zoxazolamine treatments (Hernandez et al., *Toxicol. Appl. Pharmacol.* 216:186 (2006)). Data is analyzed by Student's t-tests using StatView® software (SAS Institute Inc., Cary, N.C.), and a p-value $\leq 0.05$ will be regarded as statistically significant.

Parathion: Parathion is an organophosphate insecticide that activates CAR. It is also much more toxic to CAR-null mice than wild-type mice. Initial toxicity is outwardly shown by mucous discharge from the eyes and later by reduced activity or complete lethargy similar to other acetylcholinesterase inhibitors. Mice are injected ip with 5 mg/kg of parathion and watched for behavioral changes. Mice showing toxicity are immediately euthanized to avoid unnecessary distress or pain. Statistical differences are determined using a Fisher's 2×2 test (StatView®, SAS Institute, Cary, N.C.).

It is expected that the Cyp2b-knockdown mice treated as described herein will show increased sensitivity to the toxicants as compared to the wild-type mice. Livers from all of the treated mice will be excised, diced and frozen at −80° C. for RNA isolation and protein preparation for future analysis of Cyp2b and other P450 enzyme expression.

C. Test Whether Cyp2B Knockdowns are Resistant to the Toxicity Associated with Acetaminophen (APAP) or Other Drugs and Environmental Chemicals.

CAR-null mice show decreased sensitivity to chlorpyrifos and acetaminophen. In addition, strychnine toxicity can be investigated in Cyp2b-knockdown and wild-type mice because species differences in strychnine toxicity have been inversely correlated to Cyp2b expression levels (Oguri et al., *Arch. Biochem. Biophys.* 287:105 (1991); Yamada et al., *Arch. Biochem. Biophys.* 299:248 (1992); Tanimoto et al., *J. Pharamcobiodyn.* 13:136 (1990)). There are varying reasons for the differential toxicities, but perturbed P450 expression almost certainly plays a role. Therefore, wild-type and Cyp2b-knockdown mice are treated with chlorpyrifos, acetaminophen, and strychnine (n=5/treatment).

Acetaminophen: Wild-type and Cyp2b knockdown mice are injected ip once with 250 mg/kg of acetaminophen in sterile corn oil. Mice are euthanized 6 hours after injection (n=5). Briefly, mice are weighed, anesthetized with isoflurane for blood collection by heart puncture, and euthanized with carbon dioxide. A section of liver is excised and placed in 10% formalin (Fisher Scientific, Fair Lawn, N.J.) for histological examination as described herein. All samples are coded so that the veterinary pathologist is unaware of the sample's treatment group. In addition, serum ALT or GSTα is determined by ELISA. It is expected that the Cyp2b-knockdown mice will show less toxicity than the corresponding controls, and that TCPOBOP-treated mice will show the greatest amount of toxicity.

Chlorpyrifos: Similar to parathion, chlorpyrifos is an organophosphate insecticide that activates CAR, but chlorpyrifos is more toxic to wild-type mice. Initial toxicity is outwardly shown by mucous discharge from the eyes and later by reduced activity or complete lethargy, similar to other acetylcholinesterase inhibitors. Mice are injected ip with 10 mg/kg of chlorpyrifos and watched for behavioral changes. Mice showing toxicity are immediately euthanized to avoid unnecessary distress or pain. Statistical differences are determined using a Fisher's 2×2 test (StatView®, SAS Institute, Cary, N.C.). It is expected that the Cyp2b-knockdown mice treated as described herein will show decreased sensitivity to the toxicants as compared to the wild-type mice.

Strychnine: Strychnine is a Cyp2b-inducer (Oguri et al., *Arch. Biochem. Biophys.* 287:105 (1991); Yamada et al., *Arch. Biochem. Biophys.* 299:248 (1992)) and therefore a potential CAR agonist. Strychnine is administered ip (75 mg/kg in saline) and observed for 30 minutes. Latency time to the first convulsions and number of animals showing convulsion is noted. Mice that do not show clonic or tonic convulsion within 30 minutes are considered protected (Vasconcelos et al., *J. Ethnopharmacol.* 110:271 (2007)). It is expected that some of the Cyp2b-knockdown mice may show protection from strychnine induced convulsions. Statistical analysis is performed using Fisher's 2×2 tests.

Livers from all of the treated mice are excised, diced and frozen at −80° C. for RNA isolation and protein preparation for future analysis of Cyp2b and other P450 enzyme expression.

The foregoing is illustrative of the present invention, and is not to be construed as limiting thereof. The invention is defined by the following claims, with equivalents of the claims to be included therein. All publications, patent applications, patents, patent publications, sequences (nucleotide sequences, single polymorphism nucleotides, amino acid sequences, etc.) identified in the GenBank® database or other sequence databases and any other references cited herein are incorporated by reference in their entireties for the teachings relevant to the sentence and/or paragraph in which the reference is presented.

What is claimed is:

1. A siRNA targeted to RNAs encoding two or more enzymes of a CYP subfamily of cytochrome P450 enzymes, wherein the siRNA comprises a nucleotide sequence identical to one of SEQ ID NOS: 4-6 or a fragment thereof of at least 16 contiguous nucleotides.

2. The siRNA of claim 1, wherein the CYP subfamily is a mouse CYP subfamily.

3. The siRNA of claim 2, wherein the CYP subfamily is Cyp2b.

4. The siRNA of claim 1, wherein the siRNA has a length of about 16 to about 30 nucleotides.

5. A vector comprising a polynucleotide encoding the siRNA of claim 1.

6. A vector comprising polynucleotides encoding two or more different siRNAs of claim 1.

7. The vector of claim 5, wherein the vector is a viral vector.

8. The vector of claim 7, wherein the vector is a lentiviral vector.

9. The vector of claim 5, wherein the vector is a plasmid vector.

10. The vector of claim 5, wherein the vector encodes a short hairpin RNA (shRNA) that is processed after expression into a siRNA.

11. The vector of claim 5, further comprising a promoter operably linked to the polynucleotide encoding the siRNA.

12. The vector of claim 11, wherein said promoter is a constitutive promoter.

13. The vector of claim 12, wherein said promoter is a U6 promoter.

14. The vector of claim 12, wherein said promoter is an inducible promoter.

15. A cell comprising the siRNA of claim 1.

16. A cell comprising two or more different siRNAs of claim 1.

17. A cell comprising the vector of claim 5.

18. The cell of claim 15, wherein the cell is a mouse cell.

19. The cell of claim 15, wherein the cell is a hepatocyte.

20. A kit comprising the siRNA of claim 1.

21. A kit comprising two or more different siRNAs of claim 1.

22. A kit comprising the vector of claim 5.

23. A kit comprising the cell of claim 15.

24. A method of decreasing expression of two or more genes from a CYP subfamily in a non-human animal, comprising delivering to a cell of said animal the siRNA of claim 1.

25. The method of claim 24, wherein said animal is a mouse.

26. The method of claim 24, wherein expression of two or more genes from a CYP subfamily is decreased by at least about 50%.

27. The method of claim 24, comprising delivering at least two different siRNAs of claim 1 to a cell of said animal.

28. The method of claim 24, wherein said siRNA is delivered to the cell in the form of a vector comprising a polynucleotide encoding the siRNA.

* * * * *

UNITED STATES PATENT AND TRADEMARK OFFICE
CERTIFICATE OF CORRECTION

PATENT NO.        : 8,217,161 B2                                    Page 1 of 1
APPLICATION NO.   : 12/427791
DATED             : July 10, 2012
INVENTOR(S)       : William S. Baldwin It is certified that error appears in the above-identified patent and that said Letters Patent is hereby corrected as shown below:

In the Claims

Claim 14, column 62, line 34, "the vector of claim 12" should be changed to "The vector of claim 11"

Signed and Sealed this
Seventh Day of October, 2014

Michelle K. Lee
*Deputy Director of the United States Patent and Trademark Office*